United States Patent
Smith et al.

(10) Patent No.: US 9,914,727 B2
(45) Date of Patent: *Mar. 13, 2018

(54) FACTOR IXA INHIBITORS

(71) Applicants: Merck Sharp & Dohme Corp., Rahway, NJ (US); Mochida Pharmaceutical Co., Ltd., Tokyo (JP)

(72) Inventors: Cameron James Smith, Lawrenceville, NJ (US); John Qiang Tan, Westfield, NJ (US); Ting Zhang, Princeton Junction, NJ (US); James Balkovec, Martinsville, NJ (US); William John Greenlee, Teaneck, NJ (US); Liangqin Guo, Edison, NJ (US); Yi-Heng Chen, Whippany, NJ (US); Yili Chen, Hillsborough, NJ (US); Samuel Chackalamannil, Califon, NJ (US); Tomokazu Hirabayashi, Shizuoka Prefecture (JP); Mika Sekioka, Shizuoka Prefecture (JP)

(73) Assignees: Merck Sharp & Dohme Corp., Rahway, NJ (US); Mochida Pharmaceutical Co., Ltd., Tokyo (JP)

( * ) Notice: Subject to any disclaimer, the term of this patent is extended or adjusted under 35 U.S.C. 154(b) by 50 days.

This patent is subject to a terminal disclaimer.

(21) Appl. No.: 14/652,174

(22) PCT Filed: Dec. 16, 2013

(86) PCT No.: PCT/US2013/075232
§ 371 (c)(1),
(2) Date: Jun. 15, 2015

(87) PCT Pub. No.: WO2014/099695
PCT Pub. Date: Jun. 26, 2014

(65) Prior Publication Data
US 2015/0329562 A1    Nov. 19, 2015

Related U.S. Application Data

(60) Provisional application No. 61/739,256, filed on Dec. 19, 2012.

(51) Int. Cl.
*C07D 413/14*    (2006.01)
*C07D 413/12*    (2006.01)
*C07D 513/04*    (2006.01)

(52) U.S. Cl.
CPC ......... *C07D 413/14* (2013.01); *C07D 413/12* (2013.01); *C07D 513/04* (2013.01)

(58) Field of Classification Search
CPC ... C07D 413/12; C07D 413/14; C07D 513/04
See application file for complete search history.

(56) References Cited

U.S. PATENT DOCUMENTS

| | | |
|---|---|---|
| 2004/0220206 A1 | 11/2004 | Smallheer et al. |
| 2005/0228000 A1 | 10/2005 | Smallheer et al. |
| 2006/0293336 A1 | 12/2006 | Sutton et al. |
| 2008/0279845 A1 | 11/2008 | Conley et al. |
| 2009/0181983 A1 | 7/2009 | Corte |
| 2011/0059958 A1 | 3/2011 | Nishida et al. |
| 2011/0065682 A1 | 3/2011 | Clasby et al. |
| 2011/0135650 A1 | 6/2011 | Chackalamannil et al. |

FOREIGN PATENT DOCUMENTS

| | | |
|---|---|---|
| WO | WO2011025565 A1 | 3/2011 |
| WO | WO2014099694 | 6/2014 |
| WO | WO2014120346 A1 | 8/2014 |

OTHER PUBLICATIONS

International Search Report and Written Opinion for PCT/US13/75232 dated Apr. 21, 2014, 10 pages.
Extended European Search Report for13866418.0, dated Apr. 22, 2016, 7 pages.

*Primary Examiner* — Rebecca L Anderson
(74) *Attorney, Agent, or Firm* — Nicole M. Beeler; John C. Todaro

(57) ABSTRACT

The present invention provides compounds of Formula (I)

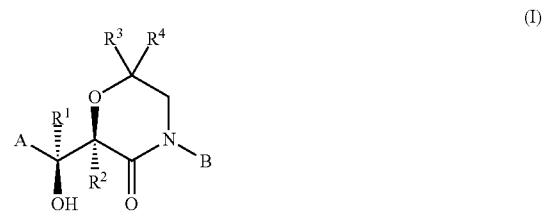

and pharmaceutical compositions comprising compounds of Formula I, and methods for using compounds of Formula I for treating or preventing thromboses, embolisms, hypercoaguability or fibrotic changes.

6 Claims, No Drawings

FACTOR IXA INHIBITORS

CROSS REFERENCE TO RELATED APPLICATIONS

This application is a U.S. National Phase application under 35 U.S.C. § 371 of PCT Application No. PCT/US13/75232 filed Dec. 16, 2013, which claims priority from U.S. Provisional Application Ser. No. 61/739,256, filed Dec. 19, 2012.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. Clotting factor IX can be activated by means of the intrinsic pathway and the extrinsic pathway. The activation of factor IXa is thus a central point of intersection between the two pathways of activation of clotting. Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445). Vijaykumar et al., *Bioorganic & Medicinal Chemistry Letters* (2006), 16 (10), 2796-2799, discloses hydroxy pyrazole based factor IXa inhibitors.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor IXa inhibitors and may have therapeutic value in, for example, preventing coronary artery disease. The invention includes compounds of formula I:

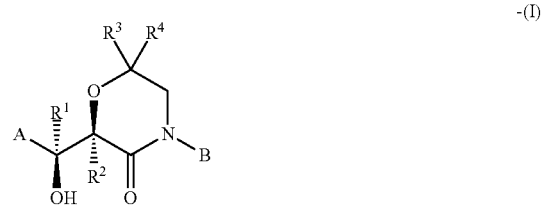

wherein
$R^1$, $R^2$, $R^3$ and $R^4$ independently H or $C_{1-6}$ alkyl, provided that when $R^1$, $R^2$, and $R^3$ are H, $R^4$ is $C_{1-6}$ alkyl, and when $R^1$, $R^2$, and $R^4$ are H, $R^3$ is $C_{1-6}$ alkyl, and when $R^1$, $R^3$, and $R^4$ are H, $R^2$ is $C_{1-6}$ alkyl, and when $R^2$, $R^3$, and $R^4$ are H, R is $C_{1-6}$ alkyl;
A is
  1) a 9-10 membered bicyclic heterocycle having 2-3 heteroatoms independently selected from N, S and O, which 9-10 membered bicyclic heterocycle is unsubstituted or substituted with =O, —C(=NH)NH$_2$, or pyrazole, or
  2) a 12-, 13-, or 14-membered tricyclic heterocycle having 3-5 heteroatoms selected from N, S and O, which 12-, 13-, or 14-membered heterocycle is unsubstituted or substituted with =O or NH$_2$;

B is
1) a 5-membered monocyclic heterocycle having 2 nitrogen atoms and 3 carbon atoms, where
   one 5-membered monocyclic heterocycle nitrogen is substituted with 6-membered monocyclic heterocycle having one or two nitrogen atoms, C$_{1-6}$ alkyl, C$_{3-8}$ carbocycle, or aryl, wherein heterocycle, alkyl, carbocycle and aryl are unsubstituted, mono-substituted, or independently di-substituted with CF$_3$, OCH$_3$, F, CN, —CHF$_2$, or =O,
   and one 5-membered monocyclic heterocycle carbon atom is unsubstituted or substituted with C$_{1-6}$ alkyl,
2) a 6-membered monocyclic heterocycle having 1 nitrogen atom and 5 carbon atoms, where one or two carbon atoms are independently unsubstituted or independently substituted with CF$_3$, —C(CH$_3$)$_2$OH, —OCHF$_2$, —CH(CF$_3$)OH, —C(CF$_3$)(CH$_3$)OH, F,

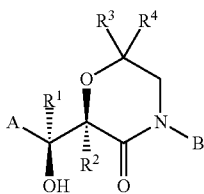

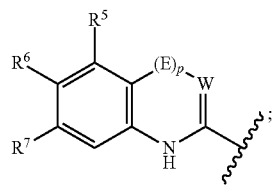

or 3) aryl, substituted with —C$_{1-6}$ alkyl.

In one embodiment of compounds of formula (I),

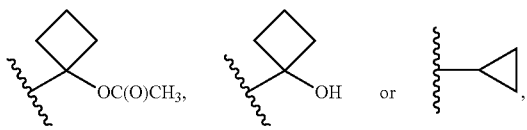

(I)

R$^1$, R$^2$, R$^3$ and R$^4$ are independently H or C$_{1-6}$ alkyl, provided that when R$^1$, R$^2$, and R$^3$ are H, R$^4$ is C$_{1-6}$ alkyl, and when R$^1$, R$^2$, and R$^4$ are H, R$^3$ is C$_{1-6}$ alkyl, and when R$^1$, R$^3$, and R$^4$ are H, R$^2$ is C$_{1-6}$ alkyl, and when R$^2$, R$^3$, and R$^4$ are H, R is C$_{1-6}$ alkyl;

A has the formula (II)

(II)

wherein
W is N or CH;
E is S(O)$_2$ or C(O);
p is 0 or 1;
R$^5$ is H or, together with R$^6$ and the atoms to which they are attached, forms a 5- or 6-membered monocyclic heterocycle having 2 heteroatoms independently selected from N, S and O, which heterocycle is substituted at a carbon atom with NH$_2$;

R$^6$ is H, —C(=NH)NH$_2$, pyrazole, or, together with R$^5$ and the atoms to which they are attached, forms a 5- or 6-membered monocyclic heterocycle, having 2 heteroatoms independently selected from N, S and O, which heterocycle is substituted at a carbon atom with NH$_2$, or, provided R$^5$ and R$^6$ do not form a heterocycle, forms, together with R$^7$ and the atoms to which they are attached, a 5-membered monocyclic heterocycle, having 2 heteroatoms independently selected from N, S and O, or forms, together with R$^7$ and the atoms to which they are attached, a 6-membered monocyclic heterocycle having 1 N atom, which 5- or 6-membered heterocycle is substituted at a carbon atom with NH$_2$;

R$^7$ is H, —C(=NH)NH$_2$, or, provided R$^5$ and R$^6$ do not form a heterocycle, forms, together with R$^6$ and the atoms to which they are attached, a 5-membered monocyclic heterocycle, having 2 heteroatoms independently selected from N, S and O, or forms, together with R$^6$ and the atoms to which they are attached, a 6-membered monocyclic heterocycle having 1 N atom, which 5- or 6-membered heterocycle is substituted at a carbon atom with NH$_2$;

provided R$^5$, R$^6$ and R$^7$ are not simultaneously H; and

B is 1) a 5-membered monocyclic heterocycle having 2 nitrogen atoms and 3 carbon atoms, where
   one 5-membered monocyclic heterocycle nitrogen is substituted with

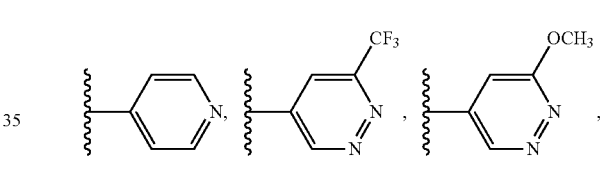

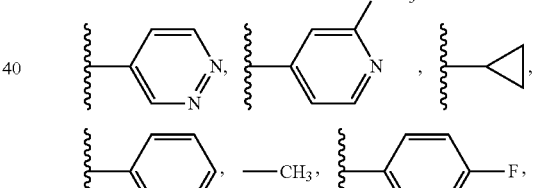

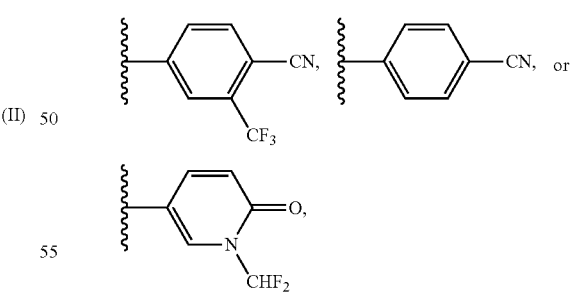

and one 5-membered monocyclic heterocycle carbon atom is unsubstituted or substituted with

—CH$_3$, 2) a 6-membered monocyclic heterocycle having 1 nitrogen atom and 5 carbon atoms, where one or two carbon atoms are independently unsubstituted or independently substituted with CF$_3$, —C(CH$_3$)$_2$OH, —OCHF$_2$, —CH(CF$_3$)OH, —C(CF$_3$)(CH$_3$)OH, F,

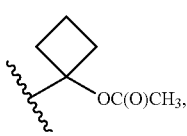 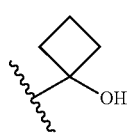 or or 3) aryl, substituted with —CH₃.

In another embodiment of compounds of formula I,

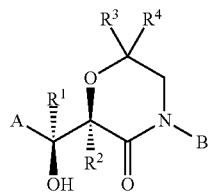
(I)

R¹, R², R³ and R⁴ are independently H or $C_{1-6}$ alkyl, provided that when R¹, R², and R³ are H, R⁴ is $C_{1-6}$ alkyl, and when R¹, R², and R⁴ are H, R³ is $C_{1-6}$ alkyl, and when R¹, R³, and R⁴ are H, R² is $C_{1-6}$ alkyl, and when R², R³, and R⁴ are H, R is $C_{1-6}$ alkyl;

A is

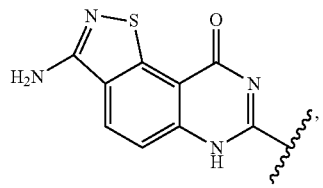

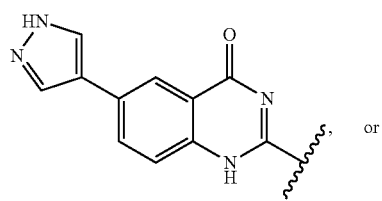 or and

B is

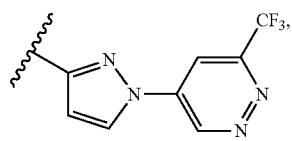

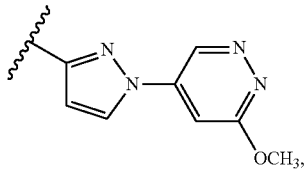

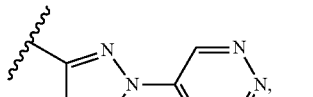

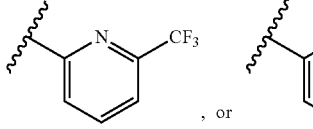

, or .

In another embodiment of compounds of formula I,

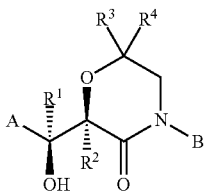
(I)

R¹, R², R³ and R⁴ are independently H or CH₃, provided that when R¹, R², and R³ are H, R⁴ is CH₃, and when R¹, R², and R⁴ are H, R³ is CH₃, and when R¹, R³, and R⁴ are H, R² is CH₃, and when R², R³, and R⁴ are H, R¹ is CH₃.

In another embodiment of the invention, the compound is (R)-2-((S)-(3-Amino-9-oxo-6,9-dihydroisothiazolo[5,4-f] quinazolin-7-yl)(hydroxy)methyl)-4-(1-(1-(difluoromethyl)-6-oxo-1,6-dihydropyridin-3-yl)-1H-pyrazol-3-yl)-2-methylmorpholin-3-one (Example 1) (FIXa Low Enzyme (102.1 nM)), (R)-2-((S)-(3-Amino-9-oxo-6,9-dihydroisothiazolo[5,4-f] quinazolin-7-yl)(hydroxy)methyl)-2-methyl-4-(1-(pyridazin-4-yl)-1H-pyrazol-3-yl)morpholin-3-one (Example 2) (FIXa Low Enzyme (8.597 nM)), (R)-2-((S)-1-(3-Amino-9-oxo-6,9-dihydroisothiazolo[5,4-f] quinazolin-7-yl)-1-hydroxyethyl)-4-(6-(trifluoromethyl) pyridin-2-yl)morpholin-3-one (Example 3) (FIXa Low Enzyme (577.9 nM)), (R)-2-((S)-(3-Amino-9-oxo-6,9-dihydroisothiazolo[5,4-f] quinazolin-7-yl)(hydroxy)methyl)-4-(6-(2-hydroxypropan-2-yl)pyridin-2-yl)-2-methylmorpholin-3-one (Example 4) (FIXa Low Enzyme (352.7 nM)), (R)-2-((S)-(5-(1H-Pyrazol-4-yl)-1H-benzo[d]imidazol-2-yl) (hydroxy)methyl)-6,6-dimethyl-4-(1-(6-(trifluoromethyl) pyridazin-4-yl)-1H-pyrazol-3-yl)morpholin-3-one (Example 5), 2-{(S)-hydroxy[(2R)-2-methyl-3-oxo-4-{1-[6-(trifluoromethyl)pyridazin-4-yl]-1H-pyrazol-3-yl}morpholin-2-yl] methyl}-6-(1H-pyrazol-4-yl)quinazolin-4(1H)-one (Example 6), (2R,6S)-2-((S)-(3-Amino-9-oxo-6,9-dihydroisothiazolo[5,4-f]quinazolin-7-yl)(hydroxy)methyl)-6-methyl-4-(1-(6-(trifluoromethyl)pyridazin-4-yl)-1H-pyrazol-3-yl)morpholin-3-one (Example 7), or (R)-2-((S)-(3-amino-9-oxo-6,9-dihydroisothiazolo[5,4-f]quinazolin-7-yl)(hydroxy)methyl)-4-(1-(6-methoxypyridazin-4-yl)-1H-pyrazol-3-yl)-6,6-dimethylmorpholin-3-one (Example 8).

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or CH$_3$ or a symbol that is an extended bond as the terminal group, e.g.

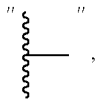

ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

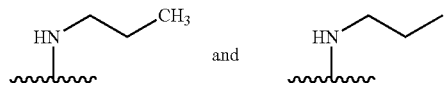

have equivalent meanings C$_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO$^-$ depending on the pH of the fluid or tissue where conversion takes place) or hydroxy form particularly in vivo and as such are encompassed within the scope of this invention. Examples of pharmaceutically acceptable pro-drug modifications include, but are not limited to, —C$_{1-6}$ alkyl esters and —C$_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted herein, alkyl groups may be unsubstituted, or substituted with 1 to 3 substituents on any one or more carbon atoms, with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$ ($C_1$-$C_6$ alkyl)-, ($C_0$-$C_6$ alkyl)C(O)NH—, $H_2$N—C(NH)—, —O($C_1$-$C_6$ alkyl)CF$_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted, the term "halogen" means fluorine, chlorine, bromine or iodine.

Except where noted, the term "aryl" refers to a stable 6- to 10-membered mono- or bicyclic ring system such as phenyl, or naphthyl. The aryl ring can be unsubstituted or substituted with one or more of $C_{1-4}$ alkyl, hydroxyl, alkoxy, halogen, or amino.

Except where noted, the term "heterocycle" refers to a stable 4- to 7-membered mono- or bicyclic- or stable 7- to 12-membered bicyclic or stable 12- to 14-membered heteroatom-containing ring system unsubstituted or substituted with $C_{1-4}$ alkyl or halogen, any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocycle is fused to a benzene ring. Especially useful are rings containing one oxygen or sulfur, one to four nitrogen atoms, or one oxygen or sulfur combined with one or two nitrogen atoms. The heterocycle may be attached at any heteroatom or carbon atom which results in the creation of a stable structure. Examples of such heterocycles include piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

Except where noted herein, the term "heteroaryl" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The term "saturated heterocycle" refers to a saturated monocyclic 5- to 8-membered ring having 1-4 heteroatoms selected from N, O and S, or a 7- to 12-membered saturated or partially saturated bicyclic ring system having 1-6 heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ carbocycle. The carbocycle may be attached to the rest of the molecule at any carbon atom which results in a stable compound. Saturated carbocyclic rings are also referred to as "cycloalkyl" rings, e.g., cyclopropyl, cyclobutyl, etc.

Except where noted herein, aryl groups and carbocycle groups may be unsubstituted, or substituted on any one or more carbon atoms, with halogen, $C_1$-$C_{20}$ alkyl, CF$_3$, NH$_2$, —NH($C_1$-$C_6$ alkyl), —N($C_1$-$C_6$ alkyl)$_2$, NO$_2$, oxo, CN, N$_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)CF$_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$ ($C_1$-$C_6$ alkyl)-, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, heteroaryl and heterocyclic rings may be unsubstituted, or substituted on any one or more carbon atoms, with halogen, $C_1$-$C_{20}$ alkyl, CF$_3$, NH$_2$, —NH($C_1$-$C_6$ alkyl), —N($C_1$-$C_6$ alkyl)$_2$, NO$_2$, oxo, CN, N$_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)CF$_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$ alkyl)OC(O)NH—, HOC(O)NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O)NH$_2$, —$C_1$-$C_6$ alkylC(O)NH$_2$, —$C_1$-$C_6$ alkylOC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

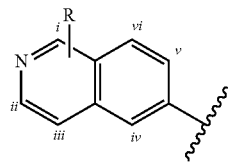

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

The invention also includes derivatives of the compound of Formula I, acting as prodrugs. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Factor IXa inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the Factor IXa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor IXa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor IXa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor IXa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The effectiveness of compounds of the present invention to inhibit the coagulation factors XIa, VIIa, IXa, Xa, plasma kallikrein or thrombin, can be determined using a relevant purified serine protease, respectively, and an appropriate synthetic substrate.

Methods for Making the Compounds of Present Invention

General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when compounds of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

Scheme 1
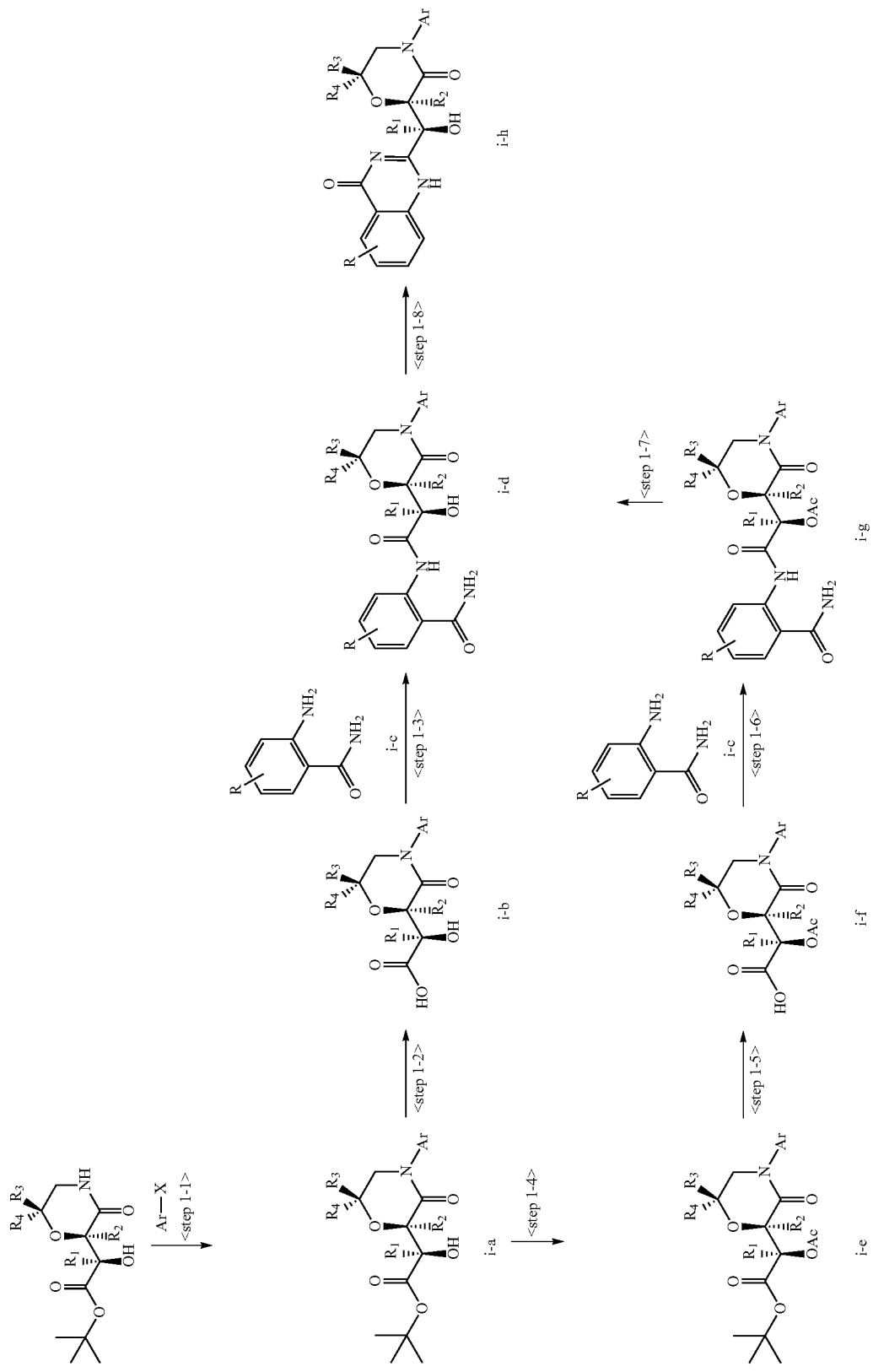

<Step 1-1>

A compound represented by formula (i-a) can be produced by allowing a key intermediate compound represented by formula (key intermediate) to react with a compound represented by Ar—X (aryl halide or heteroaryl halide, wherein X represents halogen atom) by a process known as Goldberg reaction which are similar to that described in published documents, for example, *JACS,* 2002, 124, 7421 in the presence of a base such as potassium phosphate, cesium carbonate, potassium tert-butoxide, sodium hydride, lithium hydroxide, sodium hydroxide, potassium hydroxide, lithium carbonate, sodium carbonate, or potassium carbonate in the presence of 1,2-diamine ligand such as trans-1,2-cyclohexanediamine, trans-N,N'-dimethylcyclohexane-1,2-diamine, or ethylene diamine, and in the presence of catalytic amount of cupper iodide using a solvent which is inactive to the reaction, such as an ethereal solvent, e.g., diethyl ether, tetrahydrofuran, 1,2-dimethoxyethane, 1,4-dioxane, polar solvents such as N,N-dimethylformamide, and dimethyl sulfoxide; or an aromatic hydrocarbon solvent, e.g., toluene or benzene or a mixed solvent thereof at a temperature in the range of room temperature to the solvent-reflux temperature.

<Step 1-2>

A compound represented by formula (i-b) can be produced from a compound represented by formula (i-a) by a well-known or similar process that described in published documents, for example, Jikken Kagaku Koza (Experimental Chemistry Series), 4th edition, 22, Organic synthesis IV, Acids, amino acids, and peptides, pp. 1-43, 1992, Maruzen Co., Ltd., in the presence of inorganic or organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid with water or without water and a solvent which is inactive to the reaction, such as methanol, ethanol, 2-propanol, N,N-dimethylformamide, dioxane, or tetrahydrofuran, or a mixed solvent thereof at a temperature in the range of 0° C. to the solvent-reflux temperature.

<Step 1-3>

A compound represented by formula (i-d) can be produced by allowing a compound represented by formula (i-b) to react with a compound represented by formula (i-c) (where R is, for example, —C(=NH)NH$_2$, or pyrazole) by a well-known or process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of 0° C. to the solvent-reflux temperature. When a compound represented by formula (i-b) is converted to an acid halide, a compound represented by formula (i-c) can be similarly produced by conducting a reaction by a process similar to that described in, for example, Organic synthesis IV, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

<Step 1-4>

A compound represented by formula (i-e) can be produced by allowing a compound represented by formula (i-a) to react with acetic anhydride or acetyl chloride by a well-known or process similar to that described in published documents, for example, Jikken Kagaku Koza (Experimental Chemistry Series), 4th edition, 22, Organic synthesis IV, Acids, amino acids, and peptides, pp. 191-309, 1992, Maruzen Co., Ltd.

<Step 1-5>

A compound represented by formula (i-f) can be produced by the similar process as that used in <Step 1-2> of (Reaction Scheme 1) using a compound represented by formula (i-e)

<Step 1-6>

A compound represented by formula (i-g) can be produced by the similar process as that used in <Step 1-3> of (Reaction Scheme 2) using a compound represented by formula (i-f) with a compound represented by formula (i-c).

<Step 1-7>

A compound represented by formula (i-d) can be produced by conducting a reaction using a compound represented by formula (ii-g) by a process similar to that described in published documents, for example, *Can. J. Chem.,* 49, 493 (1971) or Greene, T. W., et. al., *Protective Groups in Organic Synthesis* (2007), 4th Ed., in the presence of ammonia or hydrazine, using a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether, dioxane, or tetrahydrofuran, or a mixed solvent thereof at a temperature in the range of −78° C. to the room temperature.

<Step 1-8>

A compound represented by formula (i-h) can be produced by allowing a compound represented by formula (i-d) by a process similar to that described in published documents, for example, *European Journal of Medicinal Chemistry* 48, 231 (2012) or *Tetrahedron Asymmetry* 22, 300 (2011) in the presence of a base such as potassium tert-butoxide, sodium tert-butoxide, sodium methoxide, sodium hydride, lithium hydroxide, sodium hydroxide, potassium hydroxide, lithium carbonate, sodium carbonate, or potassium carbonate using a solvent which is inactive to the reaction, such as an alcoholic solvent, e.g., water, methanol, ethanol, 2-propanol, tert-butanol, or ethylene glycol, an ethereal solvent, e.g., diethyl ether, dioxane, or tetrahydrofuran, polar solvent, e.g., acetonitrile, N,N-dimethylformamide, or dimethyl sulfoxide, or a mixed solvent thereof at a temperature in the range of 0° C. to the solvent-reflux temperature.

Scheme 2

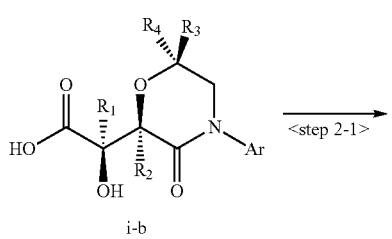

i-b

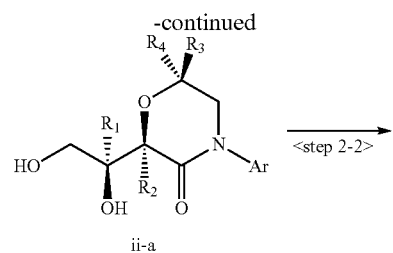

ii-a

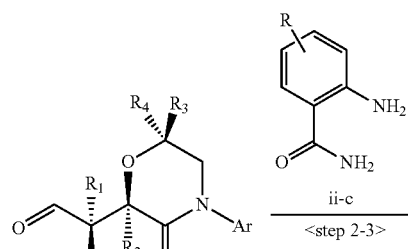

ii-b

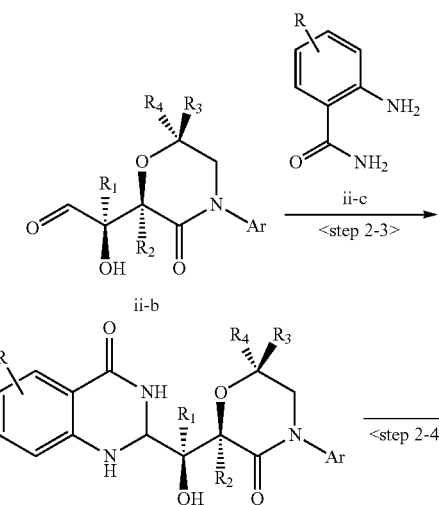

ii-d

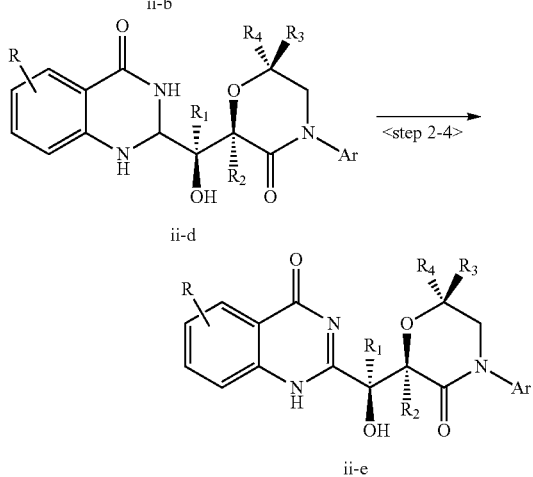

ii-e

<Step 2-1>

A compound represented by formula (ii-a) can be produced by allowing a compound represented by formula (i-b) by a well-known or process similar to that described in published documents, for example, Jikken Kagaku Koza (Experimental Chemistry Series), 5th edition, 14, Organic synthesis II, alcohol and amine, pp. 1-49, 2005, Maruzen Co., Ltd., in the presence of $LiAlH_4$, $[(MeOCH_2CH_2O)_2AlH_2]Na$, or $BH_3$ using a solvent which is inactive to the reaction, such as an ethereal solvent, e.g., diethyl ether, dioxane, or tetrahydrofuran, an aromatic hydrocarbon solvent, e.g., toluene or benzene, or a mixed solvent thereof at a temperature in the range of 0° C. to the solvent-reflux temperature.

Alternately, a compound represented by formula (ii-a) can be produced by allowing a compound represented by formula (i-b) via ester, acid chloride, or acid anhydride, by a process similar to that described in published documents, for example, Jikken Kagaku Koza (Experimental Chemistry Series), 5th edition, 16, Organic synthesis IV, Acids, amino acids, and peptides, pp. 35-70, 99-118, 2005, Maruzen Co., Ltd., and resulting ester, acid chloride, or acid anhydride compound can be reduced to alcohol by a process similar to that described in published documents, for example, Jikken Kagaku Koza (Experimental Chemistry Series), 5th edition, 14, Organic synthesis II, alcohol and amine, pp. 1-49, 2005, Maruzen Co., Ltd., in the presence of $LiAlH_4$, $[(MeOCH_2CH_2O)_2AlH_2]Na$, $BH_3$, $LiBH_4$, $NaBH_4$, $NaB(OMe)_3H$, DIBAL, $AlH_3$, $Zn(BH_4)_2$, $LiBEt_3H$, or Na using a solvent which is inactive to the reaction, such as an ethereal solvent, e.g., diethyl ether, dioxane, dimethoxyethane, or tetrahydrofuran, a halogenated solvent, e.g., dichloromethane, dichloroethane or chloroform, an aromatic hydrocarbon solvent, e.g., toluene or benzene, an alcoholic solvent, e.g., water, methanol, ethanol, 2-propanol, tert-butanol, or ethylene glycol, or a mixed solvent thereof at a temperature in the range of 0° C. to the solvent-reflux temperature.

<Step 2-2>

A compound represented by formula (ii-b) can be produced by allowing a compound represented by formula (ii-a) by a well-known or process similar to that described in published documents, for example, Jikken Kagaku Koza (Experimental Chemistry Series), 5th edition, 15, Organic synthesis III, aldehyde, ketone and quinone, pp. 9-44, 2005, Maruzen Co., Ltd., in the presence of PCC (pyridinium chlorochromate), PDC (pyridinium dichromate), $MnO_2$, Dess-Martin periodinane, IBX (2-Iodoxybenzoic acid), TEMPO (2,2,6,6-tetramethylpiperidine 1-oxyl)), or TPAP (tetrapropylammonium perruthenate) using a solvent which is inactive to the reaction, such as an ethereal solvent, e.g., diethyl ether, dioxane, or tetrahydrofuran, a halogenated solvent, e.g., dichloromethane, dichloroethane or chloroform, an aromatic hydrocarbon solvent, e.g., toluene or benzene, polar solvent, e.g., acetonitrile, N,N-dimethylformamide, or dimethyl sulfoxide, or a mixed solvent thereof at a temperature in the range of 0° C. to the solvent-reflux temperature. Alternately, a compound represented by formula (ii-b) can be produced by allowing a compound represented by formula (ii-a) by a process well-known as DMSO (dimethyl sulfoxide) oxidation such as Moffat-Swern oxidation, Moffat oxidation, Swern oxidation, $DMSO-SO_3$ pyridine oxidation or DMSO-acid anhydride oxidation that described in published documents, for example, Jikken Kagaku Koza (Experimental Chemistry Series), 5th edition, 15, Organic synthesis III, aldehyde, ketone and quinone, pp. 9-44, 2005, Maruzen Co., Ltd.

<Step 2-3>

A compound represented by formula (ii-d) can be produced from a compound represented by formula (ii-b) to react with a compound represented by formula (ii-c) (where R is $R^5$, $R^6$ or $R^7$ as defined above) by a similar process that described in published documents, for example, *European Journal of Medicinal Chemistry* 45, 4904-4913, (2010), or *JACS* 130(47), 15786 (2008), in the presence of inorganic or organic acids such as hydrochloric, hydrobromic, sulfuric, phosphoric, methanesulfonic, benzenesulfonic, p-toluenesulfonic, 10-camphorsulfonic, trifluoromethylsulfonic, acetic, oxalic, tartaric, succinic, lactic, malic, citric, fumaric, maleic, gluconic, palmitic or trifluoroacetic acid and a solvent which is inactive to the reaction, such as methanol, ethanol, 2-propanol, acetic acid, dioxane, toluene, dichloromethane, chloroform, acetonitrile, or tetrahydrofuran, or a mixed solvent thereof at a temperature in the range of 0° C. to the solvent-reflux temperature.

<Step 2-4>

A compound represented by formula (ii-e) can be produced by allowing a compound represented by formula (ii-d) by a process similar to that described in published documents, for example, *European Journal of Medicinal Chemistry* 45, 4904-4913, (2010), in the presence of $KMnO_4$, $MnO_2$, $FeCl_3$, $CuCl_2$, or DDQ (2,3-dichloro-5,6-dicyano-p-benzoquinone) using a solvent which is inactive to the reaction, such as methanol, ethanol, 2-propanol, dioxane, toluene, dichloromethane, chloroform, acetonitrile, or acetone, or a mixed solvent thereof at a temperature in the range of 0° C. to the solvent-reflux temperature.

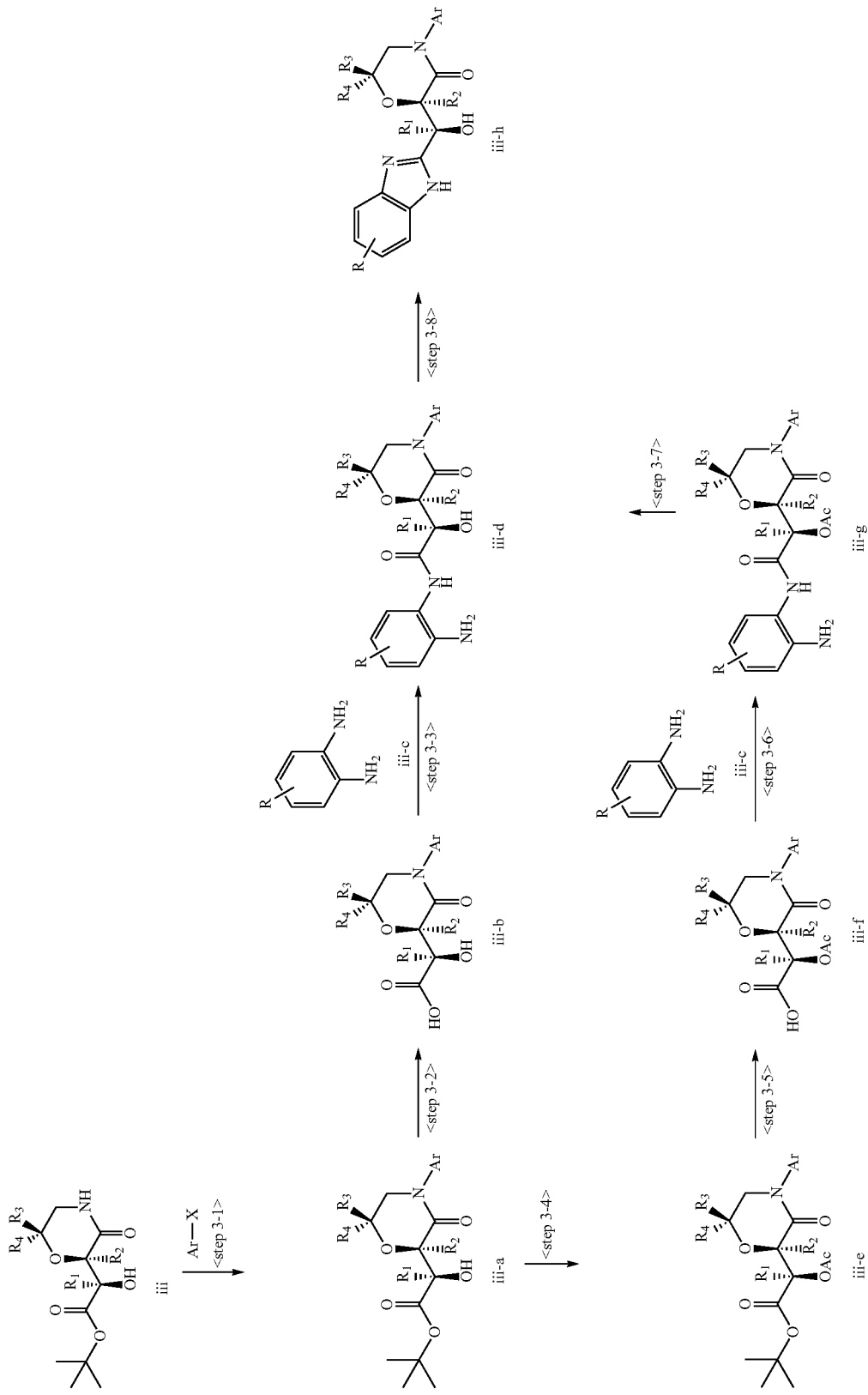

<Step 3-1>
A compound represented by formula (iii-a) can be produced by a similar process as that used in <Step 1-1> of (Reaction Scheme 1) using a compound represented by formula (iii) with a compound represented by Ar—X (aryl halide or heteroaryl halide, wherein X represents halogen atom).
<Step 3-2>
A compound represented by formula (iii-b) can be produced by a similar process as that used in <Step 1-2> of (Reaction Scheme 1) using a compound represented by formula (iii-a).
<Step 3-3>
A compound represented by formula (iii-d) can be produced by a similar process as that used in <Step 1-3> of (Reaction Scheme 1) by allowing a compound represented by formula (iii-b) to react with a compound represented by formula (iii-c) (where R is, for example, —C(=NH)NH$_2$, or pyrazole).
<Step 3-4>
A compound represented by formula (iii-e) can be produced by a similar process as that used in <Step 1-4> of (Reaction Scheme 1) by allowing a compound represented by formula (iii-a) to react with acetic anhydride or acetyl chloride.
<Step 3-5>
A compound represented by formula (iii-f) can be produced by a similar process as that used in <Step 1-2> of (Reaction Scheme 1) using a compound represented by formula (iii-e)
<Step 3-6>
A compound represented by formula (iii-g) can be produced by a similar process as that used in <Step 1-3> of (Reaction Scheme 1) using a compound represented by formula (iii-f) with a compound represented by formula (iii-c).
<Step 3-7>
A compound represented by formula (iii-d) can be produced by a similar process as that used in <Step 1-7> of (Reaction Scheme 1) by conducting a reaction using a compound represented by formula (iii-g).
<Step 3-8>
A compound represented by formula (iii-h) can be produced by exposing a compound represented by formula (iii-d) to an acid such as acetic acid at a temperature in the range of 0° C. to the solvent-reflux temperature.

EXAMPLES

The present invention will now be described in more detail using examples, but the present invention is not limited to the examples.

Acronyms and abbreviations are as follows: acetic acid (AcOH); ceric ammonium nitrate (CAN); 4-dimethylaminopyridine (DMAP); 1,2-dimethoxyethane (DME); dimethylsulfoxide (DMSO); dimethylformamide (DMF); ethanol (EtOH); ethyl acetate (EtOAc); lithium diisopropylamide (LDA); acetonitrile (MeCN); methanol (MeOH); methyl tert-butyl ether (MTBE); O-(7-Azabenzotriazol-1-yl)-N,N,N',N'-tetramethyluronium hexafluorophosphate (HATU); phenyl (Ph); tetrabutylammonium fluoride (TBAF); tetrahydrofuran (THF); trifluoroacetic acid (TFA); catalyst (cat.); anhydrous (anh.); concentrated (conc.); saturated (sat.); room temperature (RT). Celite is Celite® (Fluka) diatomite which is diatomaceous earth. Celite is Celite® (Fluka) diatomite which is diatomaceous earth.

The measurement of nuclear magnetic resonance (NMR) spectrum was performed using a JEOL JNM-ECX300 FT-NMR (manufactured by JEOL Ltd.), a JEOL JNM-ECX400 FT-NMR (manufactured by JEOL Ltd.), or a Varian Unity INOVA AS500 or AS600 FT-NMR (manufactured by Varian).

Liquid chromatography-mass spectrometry (LC-MS) was performed using a Waters FractionLynx MS system (manufactured by Waters Corporation) or a Waters Micromass ZQ Mass Spectromer/Agilent 1100 system. A SunFire Column™ (4.6 mm×5 cm, 5 micron) (manufactured by Waters Corporation) was used as an analytical column. A SunFire Column™ (19 mm×5 cm, 5 micron) (manufactured by Waters Corporation) was used as a preparative column. Methanol or MeCN and 0.05% aqueous acetic acid solution or 0.05% aqueous trifluoroacetic acid solution were used as the mobile phase. The analysis was performed under the following gradient conditions: Methanol or MeCN:0.05% aqueous acetic acid solution or 0.05% aqueous trifluoroacetic acid solution=1:9 (0 min), 10:0 (5 min), and 10:0 (6 min). Liquid chromatography-mass spectrometry (UPLC-MS) was also performed using a ACQUITY UPLC+MS system (manufactured by Waters Corporation). A CAPCELL Pak® C18 MGIII-H (2.0 mm×5 cm, 3 micron) (manufactured by Shiseido Co., Ltd.) was used as an analytical column. Methanol and 0.05% aqueous trifluoroacetic acid solution were used as the mobile phase. The analysis was performed under the following gradient conditions: Methanol:0.05% aqueous trifluoroacetic acid solution=5:95 (0 min), 95:5 (1 min), 95:5 (1.6 min), and 5:95 (2 min). The solvent systems are described as the followings: A indicates LCMS system and mobile phase is 0.05% aq. AcOH, B indicates LCMS system and mobile phase is 0.05% aq. TFA, C indicates UPLC-MS system and mobile phase is 0.05% aq. TFA.

Example 1

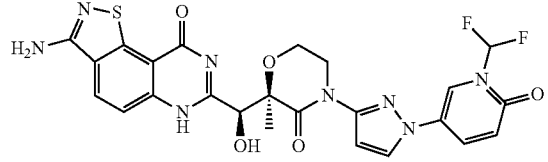

(R)-2-((S)-(3-Amino-9-oxo-6,9-dihydroisothiazolo [5,4-f]quinazolin-7-yl)(hydroxy)methyl)-4-(1-(1-(difluoromethyl)-6-oxo-1,6-dihydropyridin-3-yl)-1H-pyrazol-3-yl)-2-methylmorpholin-3-one Step 1-1: 2-Amino-6-fluorobenzamide (Compound 1-1)

A solution of 2-amino-6-fluorobenzonitrile (10.0 g) in H$_2$SO$_4$ (75.0 mL) was stirred for 1.5 h at 65° C. Then the mixture was poured into ice and brought to pH=9 by 20% NaOH aqueous solution, followed by the extraction with ethyl acetate three times. The combined organic layer were washed with brine and dried over Na$_2$SO$_4$. It was filtered to remove insoluble matters and it was concentrated in vacuo to give compound 1-1 as a pale yellow solid.

Step 1-2: 6-Amino-2-fluoro-3-iodobenzamide (Compound 1-2)

To a suspension of I$_2$ (12.4 g) and Ag$_2$SO$_4$ (15.2 g) in EtOH (420 mL) was added compound 1-1 (7.50 g), and it was stirred for 1.5 h at room temperature. Then the reaction mixture was filtered with Celite. The filtrate was concentrated in vacuo to give a crude material of compound 1-2 as a pale brown solid, which was used in the next step without further purification.

Step 1-3: 6-Amino-3-cyano-2-fluorobenzamide (Compound 1-3)

A suspension of crude compound 1-2 (16.0 g) and CuCN (6.13 g) in pyridine (210 mL) was stirred for 20 h at 120° C. The reaction mixture was cooled to room temperature, and it was filtered through a pad of Celite. The filtrate was concentrated in vacuo. The residue was purified by silica gel flash chromatography (eluent:Hexane:EtOAc=100:0~50:50) to give compound 1-3 as a yellow solid.

Step 1-4: 3,6-Diaminobenzo[d]isothiazole-7-carboxamide (Compound 1-4)

Compound 1-3 (0.40 g), sulfur (0.14 g), 25% ammonium hydroxide (2.2 ml) and 2-methoxyethanol (6.7 ml) were all taken into a sealed tube. The reaction was heated to 135° C. for 15 h. The reaction was allowed to cool down to room temperature and diluted with water and extracted with EtOAc. The organic layer was dried with anhyd. $Na_2SO_4$. Aqueous layer was concentrated in vacuo. And both crude mixture were purified by column chromatography on silica gel (Hexane:EtOAc=2:1 to EtOAc). The eluted mixture was purified again by column chromatography on silica gel using a gradient of 1-5% MeOH in $CH_2Cl_2$ to give compound 1-4 as a yellow solid.

Step 1-5: 6-Amino-3-(1,3-dioxoisoindolin-2-yl) benzo[d]isothiazole-7-carboxamide (Compound 1-5)

To a suspension of 1-4 (78 mg) in pyridine (3.7 mL), was added phthaloyl chloride (64 uL) under ice cooling and the reaction mixture was stirred at room temperature overnight. The reaction mixture was diluted with water and was extracted with EtOAc. The extract was washed with brine and dried with anhyd. $Na_2SO_4$. It was filtrated to remove insoluble matters and it was concentrated in vacuo. The residue was triturated with diethyl ether to give compound 1-5 as a yellow solid.

Step 1-6: (R)-tert-Butyl 2-hydroxy-2-((R)-4-(4-methoxybenzyl)-2-methyl-3-oxomorpholin-2-yl) acetate (Compound 1-6)

To a solution of diisopropylamine (8.29 mL) in THF (40 ml) was added 2.6M n-butyl lithium (20.0 mL) at −78° C., and stirred 10 min, warmed to 0° C. and stirred for 15 min, then cooled back to −78° C. A solution of (R)-tert-butyl 2-hydroxy-2-((R)-3-oxomorpholin-2-yl)acetate (8.29 g, WO2010065717) in THF (80 mL) was added via cannula to the cold LDA solution. The resulting reaction mixture was stirred at −78° C. for 2 h, and then methyliodide (3.67 mL) was added via syringe. This solution was slowly warmed to RT and stirred overnight. To this mixture was added sat. $NaHCO_3$, and extracted with $CH_2Cl_2$ (×3). The combined organic layer was washed with sat. $NaHCO_3$, and brine, dried over $Na_2SO_4$, filtered and concentrated in vacuo. The residue was purified by silica gel flash chromatography (eluent:Hexane:EtOAc=90:10~50:50) to give compound 1-6 as a colorless solid.

Step 1-7: (R)-tert-Butyl 2-hydroxy-2-((R)-2-methyl-3-oxomorpholin-2-yl)acetate (Compound 1-7)

To a solution of 1-6 (3.90 g) in acetonitrile (150 ml) and Water (20 ml) was added CAN (11.7 g) at 0° C. The reaction mixture was stirred for 14 h and for 3 h at 50° C. Sat. $NaHCO_3$ was added until the pH of the reaction mixture reached 4 to 5. The resulting suspension was filtered over Celite and the filter cake was washed with $CH_2Cl_2$ and then 5% MeOH in $CH_2Cl_2$. The combined organic phase was washed with brine, dried over $Na_2SO_4$, filtered and concentrated in vacuo. The residue was triturated with $CH_2Cl_2$ to give compound 1-7 as colorless solid.

Step 1-8: 5-(3-Amino-1H-pyrazol-1-yl)-1-(difluoromethyl)pyridin-2(1H)-one (Compound 1-8)

To a solution of CuI (90.6 mg) in DMSO (20 mL) was added trans-N,N'-Dimethylcyclohexane-1,2-diamine (0.15 mL) under $N_2$. The mixture was degassed under vacuum, filled with $N_2$, and it was stirred for 10 min. Then, to the reaction was added 5-bromo-1-difluoromethyl-1H-pyridin-2-one (5.20 g, Organic Letters (2006), 8(17), 3805-3808.), 3-aminopyrazole (1.93 g) and $K_3PO_4$ (9.86 g), and it was degassed. The reaction mixture was stirred for 2 h at 80° C. After cooling to room temperature, it was diluted with 1% $NH_3$ aq. and extracted with EtOAc (4 times). The combined organic layer was washed with brine, dried over $Na_2SO_4$, filtered and concentrated in vacuo. The residue was purified by silica gel flash chromatography (eluent:Hexane:EtOAc=60:40~30:70) to give compound 1-8 as a yellow solid.

Step 1-9: 1-(Difluoromethyl)-5-(3-iodo-1H-pyrazol-1-yl)pyridin-2(1H)-one (Compound 1-4)

To a solution of 1-8 (1.15 g) in MeCN (30 mL) was added concentrated $H_2SO_4$ (0.68 mL) and $NaNO_2$ (0.70 g) in water (3 mL) at 0° C. After stirring for 10 min at 0° C., KI (3.38 g) in water (4 mL) was added to the reaction at the same temperature. The reaction mixture was stirred for 1 h at room temperature and for 20 min at 40° C. It was diluted with water and extracted with EtOAc. The organic layer was washed with sat. $Na_2S_2O_3$ aq., sat. $NaHCO_3$ aq. and brine, dried over $Na_2SO_4$, filtered and concentrated. The residue was purified by silica gel flash chromatography (eluent: Hexane:EtOAc=90:10~50:50) to give compound 1-9 as a colorless solid.

Step 1-10: (R)-tert-Butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate (Compound 1-10)

According to Step 1-8 in the synthetic method for EXAMPLE 1, compound 1-9 (0.59 g) and compound 1-7 (0.43 g) were used instead of 5-bromo-1-difluoromethyl-1H-pyridin-2-one and 3-aminopyrazole to obtain compound 1-10 as a brown solid.

Step 1-11: (R)-tert-Butyl 2-acetoxy-2-((R)-4-(1-(1-(difluoromethyl)-6-oxo-1,6-dihydropyridin-3-yl)-1H-pyrazol-3-yl)-2-methyl-3-oxomorpholin-2-yl) acetate (Compound 1-11)

To a solution of compound 1-10 (0.50 g) and DMAP (14 mg) in $CH_2Cl_2$ (20 mL), were added pyridine (0.23 mL) and acetic anhydride (0.26 mL) at 0° C. and stirred for 3 h at 35° C. The reaction mixture was diluted with sat. $NaHCO_3$ aq. and extracted with $CH_2Cl_2$. The extract was washed with brine and dried over $Na_2SO_4$, filtered and concentrated in vacuo. The residue was purified by silica gel flash chromatography (eluent:Heptane:EtOAc=70:30~40:60) to give compound 1-11 as a pale yellow amorphous solid.

Step 1-12: (R)-2-Acetoxy-2-((R)-4-(1-(1-(difluoromethyl)-6-oxo-1,6-dihydropyridin-3-yl)-1H-pyrazol-3-yl)-2-methyl-3-oxomorpholin-2-yl)acetic acid (Compound 1-12)

A solution of compound 1-11 (0.40 g) in 4M HCl-dioxane (16 mL) was stirred for 17 h at 50° C. The organic solvent was evaporated under reduced pressure to afford the desired compound 1-12 as a pale yellow solid, which was used in the next step without further purification.

Step 1-13: (R)-2-((7-Carbamoyl-3-(1,3-dioxoisoindolin-2-yl)benzo[d]isothiazol-6-yl)amino)-1-((R)-4-(1-(1-(difluoromethyl)-6-oxo-1,6-dihydropyridin-3-yl)-1H-pyrazol-3-yl)-2-methyl-3-oxomorpholin-2-yl)-2-oxoethyl acetate (Compound 1-13)

To a suspension of 1-13 (240 mg) in $CH_2Cl_2$ (5 mL) were added DMF (cat.) and oxalyl chloride (150 uL) at 0° C. and stirred at room temperature for 1 h. The reaction mixture was concentrated and dissolved in $CH_2Cl_2$ (3 mL) again, and added dropwise to a solution of 1-5 (92 mg) and DMAP (6.6 mg) in pyridine (3 mL) at 0° C. The mixture was stirred for 1 h at room temperature. The reaction mixture was diluted with sat. $NaHCO_3$ aq. and extracted with EtOAc (3 times). The combined extracts were washed with brine and dried over $Na_2SO_4$, filtered and concentrated in vacuo. The residue was purified by silica gel flash chromatography (eluent: Heptane:EtOAc=70:30~10:90) to give compound 1-13 as a pale brown powder.

Step 1-14: (R)-2-((S)-(3-Amino-9-oxo-6,9-dihydroisothiazolo[5,4-f]quinazolin-7-yl)(hydroxy)methyl)-4-(1-(1-(difluoromethyl)-6-oxo-1,6-dihydropyridin-3-yl)-1H-pyrazol-3-yl)-2-methylmorpholin-3-one To a solution of 1-13 (73 mg) in $CH_2Cl_2$ (2 mL) and MeOH (2 mL), hydrazine hydrate (93.2 uL) was added and stirred for 2.5 h at room temperature. The reaction mixture was diluted with water and extracted with EtOAc (3 times). The combined extracts were washed with brine and dried over $Na_2SO_4$, filtered and concentrated in vacuo. To a suspension of the resulting solid (48 mg) in acetonitrile (2 mL) and DMF (2 mL), $K_2CO_3$ (56.3 mg) was added and stirred at 40° C. for 17 h. The reaction mixture was diluted with sat. $NH_4Cl$ aq. and extracted with EtOAc (3 times). The combined extracts were washed with brine and dried over $Na_2SO_4$, filtered and concentrated in vacuo. The residue was purified by NH-silica gel flash chromatography (eluent: $CH_2Cl_2$:MeOH=95:5~85:15) to give EXAMPLE 1 as a colorless solid.

Example 2

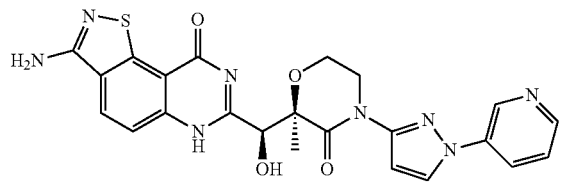

(R)-2-((S)-(3-Amino-9-oxo-6,9-dihydroisothiazolo[5,4-f]quinazolin-7-yl)(hydroxy)methyl)-2-methyl-4-(1-(pyridazin-4-yl)-1H-pyrazol-3-yl)morpholin-3-one

Step 2-1: 4-(3-Iodo-1H-pyrazol-1-yl)pyridazine (compound 2-1)

To a solution of 3-iodo-1H-pyrazole (0.75 g) in DMSO (19 mL), was added 60% NaH (0.39 g) under ice cooling and stirred for 10 min. 4-bromopyridazine hydrobromide (1.4 g) was added and stirred at room temperature for 3 days. Then 60% NaH (0.16 g) was added at 0° C. and warmed to room temperature and stirred for 1 day. The reaction mixture was diluted with water and EtOAc. The mixture was filtered with Celite, and extracted with EtOAc. The combined organic layer was washed with brine and dried with anhyd. $Na_2SO_4$. It was filtered to remove insoluble matters and it was concentrated in vacuo. The residue was triturated (Hexane:EtOAc=1:1) to obtain compound 2-1 as a brown solid.

Step 2-2: (R)-tert-Butyl 2-hydroxy-2-((R)-2-methyl-3-oxo-4-(1-(pyridazin-4-yl)-1H-pyrazol-3-yl)morpholin-2-yl)acetate (compound 2-2)

According to Step 1-8 in the synthetic method for EXAMPLE 1, compound 2-1 (0.40 g) and compound 1-7 (0.38 g) were used instead of 5-bromo-1-difluoromethyl-1H-pyridin-2-one and 3-aminopyrazole to obtain compound 2-2 as a pale brown solid.

Step 2-3: (R)-tert-Butyl 2-acetoxy-2-((R)-2-methyl-3-oxo-4-(1-(pyridazin-4-yl)-1H-pyrazol-3-yl)morpholin-2-yl)acetate (compound 2-3)

According to Step 1-11 in the synthetic method for EXAMPLE 1, compound 2-2 (0.18 g) was used instead of compound 1-10 to obtain compound 2-3 as a brown solid.

Step 2-4: (R)-2-Acetoxy-2-((R)-2-methyl-3-oxo-4-(1-(pyridazin-4-yl)-1H-pyrazol-3-yl)morpholin-2-yl)acetic acid hydrochloride (compound 2-4)

According to Step 1-12 in the synthetic method for EXAMPLE 1, compound 2-3 (0.18 g) was used instead of compound 1-11 to obtain compound 2-4 as a brown solid.

Step 2-5: (R)-2-((7-Carbamoyl-3-(1,3-dioxoisoindolin-2-yl)benzo[d]isothiazol-6-yl)amino)-1-((R)-2-methyl-3-oxo-4-(1-(pyridazin-4-yl)-1H-pyrazol-3-yl)morpholin-2-yl)-2-oxoethyl acetate (compound 2-5)

According to Step 1-13 in the synthetic method for EXAMPLE 1, compound 2-4 (0.22 g) was used instead of compound 1-12 to obtain compound 2-5 as a brown solid.

Step 2-6: (R)-2-((S)-(3-Amino-9-oxo-6,9-dihydroisothiazolo[5,4-f]quinazolin-7-yl)(hydroxy)methyl)-2-methyl-4-(1-(pyridazin-4-yl)-1H-pyrazol-3-yl)morpholin-3-one According to Step 1-14 in the synthetic method for EXAMPLE 1, compound 2-5 (48 mg) was used instead of compound 1-13 to obtain EXAMPLE 2 as a brown solid.

Example 3

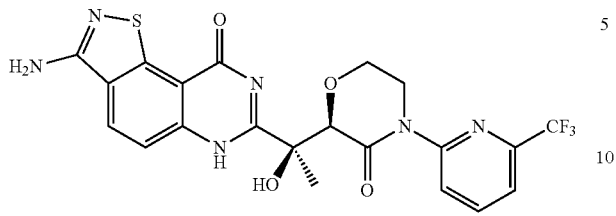

(R)-2-((S)-1-(3-Amino-9-oxo-6,9-dihydroisothiazolo[5,4-f]quinazolin-7-yl)-1-hydroxyethyl)-4-(6-(trifluoromethyl)pyridin-2-yl)morpholin-3-one

Step 3-1: (R)-tert-Butyl 2-hydroxy-2-((R)-3-oxo-4-(6-(trifluoromethyl)pyridin-2-yl)morpholin-2-yl)propanoate (compound 3-1)

According to Step 1-8 in the synthetic method for EXAMPLE 1, 2-iodo-6-(trifluoromethyl)pyridine (0.50 g) and (R)-tert-butyl 2-hydroxy-2-((R)-3-oxomorpholin-2-yl)propanoate (0.45 g) were used instead of 5-bromo-1-difluoromethyl-1H-pyridin-2-one and 3-aminopyrazole to obtain compound 3-1 as a colorless solid.

Step 3-2: (R)-2-Hydroxy-2-((R)-3-oxo-4-(6-(trifluoromethyl)pyridin-2-yl)morpholin-2-yl)propanoic acid hydrochloride (compound 3-2)

According to Step 1-12 in the synthetic method for EXAMPLE 1, compound 3-1 (0.44 g) was used instead of compound 1-11 to obtain compound 3-2 as a colorless solid.

Step 3-3: (1-Chloroethyl carbonic) (R)-2-hydroxy-2-((R)-3-oxo-4-(6-(trifluoromethyl)pyridin-2-yl)morpholin-2-yl)propanoic anhydride (compound 3-3)

To a suspension of compound 3-2 (0.13 g) in $CH_2Cl_2$ (3.5 mL), were added triethylamine (0.15 mL) and 1-chloroethyl chloroformate (0.11 mL) at 0° C. and stirred at room temperature overnight. The reaction mixture was diluted with water and extracted with $CH_2Cl_2$. The extract was washed with brine and dried with anh. $Na_2SO_4$. It was filtrated to remove insoluble matters and it was concentrated in vacuo to give compound 3-3.

Step 3-4: (R)-2-((S)-1,2-Dihydroxypropan-2-yl)-4-(6-(trifluoromethyl)pyridin-2-yl)morpholin-3-one (compound 3-4)

To a solution of compound 3-3 (0.19 g) in MeOH (4.4 mL), was added sodium borohydride (33 mg) at 0° C. and stirred at room temperature for 2 h.
The reaction mixture was quenched with water and extracted with EtOAc. The extract was washed with brine, and dried with anhyd. $Na_2SO_4$. It was filtered to remove insoluble matters and concentrated in vacuo. The residue was purified by silica gel flash chromatography (eluent: Heptane:EtOAc=2:1~1:1) to obtain compound 3-4 as a colorless oil.

Step 3-5: (R)-2-Hydroxy-2-((R)-3-oxo-4-(6-(trifluoromethyl)pyridin-2-yl)morpholin-2-yl)propanal (compound 3-5)

To a solution of compound 3-4 (60 mg), DMSO (93 uL) and triethylamine (0.18 mL) in $CH_2Cl_2$ (1.9 mL) was added pyridine-sulfur trioxide complex (0.15 g) at 0° C. and stirred at room temperature for 6.5 h. The reaction mixture was poured into sat. $NH_4Cl$ and extracted with $CH_2Cl_2$. Combined organic layer was washed with and brine and dried over $Na_2SO_4$. It was filtrated to remove insoluble matters and it was concentrated in vacuo to give compound 3-5 as pale yellow oil, which was used for next step without further purification.

Step 3-6: (2R)-2-((1S)-1-(3-Amino-9-oxo-6,7,8,9-tetrahydroisothiazolo[5,4-f]quinazolin-7-yl)-1-hydroxyethyl)-4-(6-(trifluoromethyl)pyridin-2-yl)morpholin-3-one (compound 3-6)

A mixture of compound 1-4 (40 mg) and 3-5 (60 mg) in acetic acid (2 mL) was stirred at room temperature for 22 h. The reaction mixture was quenched with sat. $NaHCO_3$ and extracted with EtOAc. The extract was washed with brine and dried with anh. $Na_2SO_4$. It was filtrated to remove insoluble matters and concentrated in vacuo. The residue was purified by silica gel flash chromatography (eluent: $CH_2Cl_2$:MeOH=99:1~95:5) to give compound 3-6 as a pale yellow oil.

Step 3-7: (R)-2-((S)-1-(3-Amino-9-oxo-6,9-dihydroisothiazolo[5,4-f]quinazolin-7-yl)-1-hydroxyethyl)-4-(6-(trifluoromethyl)pyridin-2-yl)morpholin-3-one To a solution of compound 3-6 (22 mg) in $CH_2Cl_2$ (8 mL) was added $MnO_2$ (0.20 g) and stirred for 1.5 h. The reaction mixture was diluted with acetone and filtered through a pad of Celite, and concentrated in vacuo. The residue was purified by NH silica gel flash chromatography (eluent: $CH_2Cl_2$:MeOH=95:5~90:10) to give EXAMPLE 3 as a pale yellow solid.

Example 4

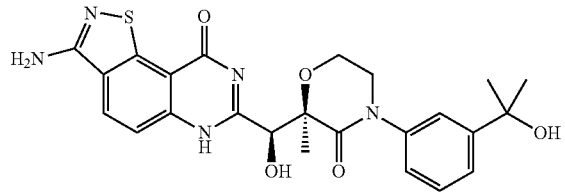

(R)-2-((S)-(3-Amino-9-oxo-6,9-dihydroisothiazolo[5,4-f]quinazolin-7-yl)(hydroxy)methyl)-4-(6-(2-hydroxypropan-2-yl)pyridin-2-yl)-2-methylmorpholin-3-one

Step 4-1: 2-(6-Bromopyridin-2-yl)propan-2-ol (compound 4-1)

Place a 1.6 M solution of n-BuLi in hexane (5.2 mL) in a dry 100 mL round bottomed flask fitted with a stir bar, septum and temperature probe. Cool in a dry-ice acetone bath to −76° C. Add THF (5 mL) to the solution, then add a solution of 2,6-dibromopyridine (2.0 g) in THF (10 mL) slowly via syringe maintaining the temperature below −60° C. Stir the solution for 30 min in the dry-ice bath, then add acetone (13.5 mL). Stir the solution in the dry-ice bath for 15 min then allow the reaction to warm to room temperature. After 1 h the reaction mixture was quenched with a 5% aqueous solution of $NH_4Cl$, and extracted with EtOAc. The combined organic layer was washed with brine and dried over Na₂SO₄. It was filtered and concentrated in vacuo. The residue was purified by silica gel column chromatography (Heptane:CH₂Cl₂=70:30 to CH₂Cl₂) to obtain compound 4-1 as an orange oil.

Step 4-2: (R)-tert-Butyl 2-hydroxy-2-((R)-4-(6-(2-hydroxypropan-2-yl)pyridin-2-yl)-2-methyl-3-oxomorpholin-2-yl)acetate (compound 4-2)

According to Step 1-8 in the synthetic method for EXAMPLE 1, compound 4-1 (0.35 g) and compound 1-7 (0.30 g) were used instead of 5-bromo-1-difluoromethyl-1H-pyridin-2-one and 3-aminopyrazole to obtain compound 2-2 as a colorless oil.

Step 4-3: (R)-tert-Butyl 2-acetoxy-2-((R)-4-(6-(2-hydroxypropan-2-yl)pyridin-2-yl)-2-methyl-3-oxomorpholin-2-yl)acetate (compound 4-3)

According to Step 1-11 in the synthetic method for EXAMPLE 1, compound 4-2 (0.32 g) was used instead of compound 1-10 to obtain compound 4-3 as a colorless oil.

Step 4-4: (R)-2-Acetoxy-2-((R)-4-(6-(2-hydroxypropan-2-yl)pyridin-2-yl)-2-methyl-3-oxomorpholin-2-yl)acetic acid hydrochloride (compound 4-4)

According to Step 1-12 in the synthetic method for EXAMPLE 1, compound 4-3 (0.35 g) was used instead of compound 1-11 to obtain compound 4-4 as a colorless solid.

Step 4-5: (R)-2-((7-Carbamoyl-3-(1,3-dioxoisoindolin-2-yl)benzo[d]isothiazol-6-yl)amino)-1-((R)-4-(6-(2-hydroxypropan-2-yl)pyridin-2-yl)-2-methyl-3-oxomorpholin-2-yl)-2-oxoethyl acetate (compound 4-5)

According to Step 1-13 in the synthetic method for EXAMPLE 1, compound 4-4 (0.20 g) was used instead of compound 1-12 to obtain compound 4-5 as a yellow solid.

Step 4-6: (R)-2-((S)-(3-Amino-9-oxo-6,9-dihydroisothiazolo[5,4-f]quinazolin-7-yl)(hydroxy)methyl)-4-(6-(2-hydroxypropan-2-yl)pyridin-2-yl)-2-methylmorpholin-3-one According to Step 1-14 in the synthetic method for EXAMPLE 1, compound 4-5 (50 mg) was used instead of compound 1-13 to obtain EXAMPLE 4 as a pale yellow solid.

TABLE 1

| EXAMPLE | NMR (ppm) |
|---|---|
| 1-1 | DMSO-d₆: 7.60-7.42 (2H, m), 7.11-7.01 (1H, m), 6.49 (1H, d, J = 8 Hz), 6.34-6.25 (1H, m), 6.15 (2H, s) |
| 1-2 | *DMSO-d₆: 7.75-7.53 (2H, m), 7.40 (1H, dd, J = 9, 7 Hz), 6.90-6.46 (2H, m), 6.40 (1H, dd, J = 9, 1 Hz) |
| 1-3 | DMSO-d₆: 7.90-7.72 (2H, m), 7.45 (1H, dd, J = 9, 8 Hz), 6.99 (2H, m), 6.58 (1H, d, J = 9 Hz) |
| 1-4 | DMSO-d₆: 7.77 (1H, d, J = 9 Hz), 7.35 (2H, s), 6.81-6.73 (1H, m), 6.43-6.26 (4H, m) |
| 1-5 | *DMSO-d₆: 8.11-7.92 (4H, m), 7.78 (1H, d, J = 9 Hz), 7.66-7.56 (2H, m), 6.95 (1H, d, J = 9 Hz), 6.66-6.54 (2H, m) |
| 1-6 | *CDCl₃: 7.22 (2H, d, J = 9 Hz), 6.86 (2H, d, J = 9 Hz), 4.70-4.60 (1H, m), 4.51 (1H, d, J = 14 Hz ), 4.32 (1H, d, J = 9 Hz), 3.96-3.77 (6H, m), 3.42-3.31 (1H, m), 3.04 (1H, dt, J = 12, 3 Hz), 1.60 (3H, s), 1.51 (9H, s) |

TABLE 1-continued

| EXAMPLE | NMR (ppm) |
|---|---|
| 1-7 | *CDCl₃: 6.12 (1H, br s), 4.27 (1H, d, J = 9 Hz), 4.02-3.83 (3H, m), 3.61-3.50 (1H, m), 3.31-3.22 (1H, m), 1.58 (3H, s), 1.51 (9H, s) |
| 1-8 | *CDCl₃: 7.73-7.67 (2H, m), 7.70 (1H, t, J = 60 Hz), 7.48-7.45 (1H, m), 6.68-6.61 (1H, m), 5.84 (1H, d, J = 2 Hz), 3.82 (2H, s) |
| 1-9 | CDCl₃: 7.81 (1H, d, J = 3 Hz), 7.75 (1H, dd, J = 10, 3 Hz), 7.69 (1H, t, J = 60 Hz), 7.56-7.53 (1H, m), 6.68 (1H, d, J = 10 Hz), 6.63 (1H, d, J = 3 Hz) |
| 1-11 | CDCl₃: 7.79-7.74 (2H, m), 7.72 (1H, t, J = 60 Hz), 7.67 (1H, d, J = 3 Hz), 7.12 (1H, d, J = 3 Hz), 6.69 (1H, d, J = 11 Hz), 5.30 (1H, s), 4.36-4.28 (1H, m), 4.20-3.97 (3H, m), 2.06 (3H, s), 1.73 (3H, s), 1.52 (9H, s) |
| 1-12 | *DMSO-d₆: 13.36 (1H, s), 8.39 (1H, d, J = 2 Hz), 8.18-8.10 (2H, m), 7.91 (1H, t, J = 59 Hz), 6.92 (1H, d, J = 2 Hz), 6.72 (1H, d, J = 10 Hz), 5.10 (1H, s), 4.21-3.94 (4H, m), 1.98 (3H, s), 1.62 (3H, s) |
| 1-13 | *CDCl₃: 11.14 (1H, s), 8.70 (1H, d, J = 9 Hz), 8.07-7.51 (9 H, m), 7.11 (1H, d, J = 3 Hz), 6.73-6.65 (1H, m), 6.17 (2H, s), 5.61 (1H, s), 4.31-4.01 (4H, m), 2.19 (3H, s), 1.77 (3H, s) |
| 1 | *DMSO-d₆: 8.43-8.32 (2H, m), 8.19-7.69 (3H, m), 7.63-7.52 (1H, m), 7.03 (1H, d, J = 2 Hz), 6.86-6.67 (3H, m), 4.89-4.78 (1H, m), 4.30-4.16 (1H, m), 4.08-3.90 (3H, m), 1.57-1.47 (3H, m) |
| 2-1 | DMSO-d₆: 9.81-9.78 (1H, m), 9.30-9.28 (1H, m), 8.72 (1H, d, J = 3 Hz), 8.05 (1H, dd, J = 6, 3 Hz), 6.96 (1H, d, J = 3 Hz) |
| 3-3 | CDCl₃: 8.37-8.29 (1H, m), 7.95-7.85 (1H, m), 7.56-7.49 (1H, m), 6.62 (1H, q, J = 6 Hz), 4.64 (1H, s), 4.55-4.48 (1H, m), 4.06-3.94 (3H, m), 1.98 (3H, s), 1.81 (3H, d, J = 6 Hz) |
| 3-4 | CDCl₃: 8.23 (1H, d, J = 8 Hz), 7.87 (1H, dd, J = 8, 8 Hz), 7.54-7.48 (1H, m), 5.24 (1H, s), 4.52-4.43 (1H, m), 4.31-4.22 (1H, m), 4.17 (1H, s), 4.00-3.76 (3H, m), 3.56 (1H, d, J = 11 Hz), 1.31 (3H, s) |
| 3-5 | CDCl₃: 9.54 (1H, s), 8.27-8.21 (1H, m), 7.88 (1H, dd, J = 8, 8 Hz), 7.56-7.49 (1H, m), 4.45-4.39 (1H, m), 4.31 (1H, s), 4.28-4.22 (1H, m), 4.04-3.90 (2H, m), 1.52 (3H, s) |
| 3-6 | DMSO-d₆: 8.33-8.25 (1H, m), 8.17-8.08 (1H, m), 7.83-7.71 (2H, m), 7.52-7.06 (1H, m), 6.82-6.68 (1H, m), 6.40-6.29 (1H, m), 5.38-5.28 (1H, m), 5.20-5.09 (1H, m), 4.50-4.41 (1H, m), 4.33-3.82 (4H, m), 1.30-1.25 (3H, m) |
| 3 | CD₃OD: 8.30-8.19 (2H, m), 7.97 (1H, dd, J = 8, 8 Hz), 7.64-7.56 (2H, m), 4.72 (1H, s), 4.32-4.16 (3H, m), 4.03-3.91 (1H, m), 1.85 (3H, s) |
| 4-1 | CDCl₃: 7.55 (1H, dd, J = 8, 8 Hz), 7.37 (1H, d, J = 8 Hz), 7.35 (1H, d, J = 8 Hz), 4.08 (1H, s), 1.55 (6H, s) |

(No mark: 400M Hz, *: 300M Hz)

TABLE 2

| | LC/MS | | |
|---|---|---|---|
| Example | m/z [M + 1]⁺ | RT min | Method/ Solvent |
| 1-4 | 209 | 0.42 | A |
| 1-5 | 339 | 3.97 | A |
| 1-6 | 388[M + Na]⁺ | 1.02 | C |
| 1-7 | 268[M + Na]⁺ | 0.80 | C |
| 1-8 | 227 | 0.55 | C |
| 1-9 | 338 | 0.94 | C |

TABLE 2-continued

| | LC/MS | | |
|---|---|---|---|
| Example | m/z [M + 1]$^+$ | RT min | Method/ Solvent |
| 1-10 | 477[M + Na]$^+$ | 1.01 | C |
| 1-11 | 519[M + Na]$^+$ | 1.03 | C |
| 1-12 | 463[M + Na]$^+$ | 0.82 | C |
| 1-13 | 761 | 0.99 | C |
| 1 | 571 | 0.92 | C |
| 2-1 | 273 | 3.80 | A |
| 2-2 | 390 | 0.94 | C |
| 2-3 | 432 | 0.98 | C |
| 2-4 | 376 | 0.71 | C |
| 2-5 | 696 | 0.94 | C |
| 2 | 506 | 0.84 | C |
| 3-1 | 413[M + Na]$^+$ | 1.1 | C |
| 3-2 | 357[M + Na]$^+$ | 0.89 | C |
| 3-4 | 343[M + Na]$^+$ | 0.9 | C |
| 3-6 | 509 | 0.83 | C |
| 3 | 507 | 0.99 | C |
| 4-2 | 381 | 0.98 | C |
| 4-3 | 445[M + Na]$^+$ | 1.02 | C |
| 4-4 | 389[M + Na]$^+$ | 0.77 | C |
| 4-5 | 687[M + Na]$^+$ | 0.97 | C |
| 4 | 519[M + Na]$^+$ | 0.88 | C |

Intermediate 1

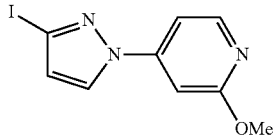 [SMILES: COc1cc(-n2ccc(I)n2)ccn1]

4-(3-Iodo-1H-pyrazol-1-yl)-2-methoxypyridine

To 3-iodo-1H-pyrazole (763 mg, 3.93 mmol) in DMSO (15 mL) at 0° C., was added sodium hydride (60% in mineral oil, 189 mg, 4.72 mmol). The reaction was warmed to 25° C. and stirred for 60 min before 4-fluoro-2-methoxypyridine (500 mg, 3.93 mmol) was added. The reaction mixture was stirred at 90° C. for 4.5 h before quenching by the addition of water. The reaction mixture was extracted with EtOAc. The combined organic extracts were dried over MgSO$_4$ and concentrated in vacuo. The crude mixture was purified by flash chromatography (ISCO Combiflash, 0-30% EtOAc in hexanes) to afford 4-(3-iodo-1H-pyrazol-1-yl)-2-methoxypyridine, as a white solid. LCMS calc.=301.97. found=302.02 (M+H)$^+$.

Intermediate 2

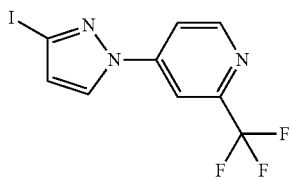 [SMILES: FC(F)(F)c1cc(-n2ccc(I)n2)ccn1]

4-(3-Iodo-1H-pyrazol-1-yl)-2-(trifluoromethyl)pyridine

To a solution of 3-iodopyrazole (0.70 g, 3.61 mmol), in DMSO (18.0 mL) was added sodium hydride (60% disp. in oil, 0.173 g, 4.33 mmol), and the resulting mixture was stirred for 0.5 h before adding 4-fluoro-2-trifluoromethyl pyridine (0.596 g, 3.61 mmol). The reaction mixture was stirred at 90° C. for 3 h. The reaction was quenched by the addition of water and extracted with EtOAc. The combined organic extracts were washed with water and brine, dried over MgSO$_4$ and concentrated in vacuo. The crude mixture was purified by flash chromatography (ISCO, 40 g, 0-50% EtOAc in hexanes) to afford 4-(3-iodo-1H-pyrazol-1-yl)-2-(trifluoromethyl)pyridine, as a white solid. LCMS calc.=339.95. found=339.93 (M+H)$^+$. $^1$H NMR (500 MHz, CDCl$_3$): δ 8.77 (d, J=5.3 Hz, 1H); 8.03 (d, J=3.8 Hz, 1H); 7.91 (d, J=2.6 Hz, 1H); 7.77 (d, J=5.4 Hz, 1H); 6.74 (d, J=2.5 Hz, 1H).

Intermediate 3

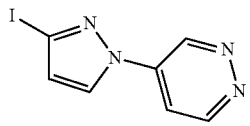 [SMILES: Ic1ccn(-c2ccnnc2)n1]

4-(3-Iodo-1H-pyrazol-1-yl)pyridazine

To the stirred solution of 4-iodopyridazine (1000 mg, 4.85 mmol) and 3-iodo-1H-pyrazole (951 mg, 4.90 mmol) in DMSO was added NaH (60% in oil, 233 mg, 5.83 mmol) in portion at 0° C. The mixture was stirred at room temperature for 30 min or until bubbling ceased, then warmed up to 50° C. and stirred at 50° C. overnight. The reaction mixture was cooled to room temperature, partitioned between EtOAc and water. The aqueous was extracted with EtOAc for three times. The organic phases were combined, dried over Na$_2$SO$_4$ and concentrated in vacuo to give the crude product. This was purified by flash chromatography (Isco Combi-Flash, 80 g Silica gel column, 0-100% EtOAc in hexanes) to afford 4-(3-iodo-1H-pyrazol-1-yl)pyridazine. LCMS calc.=272.96. found=272.96 (M+H)$^+$. $^1$H NMR (500 MHz, CDCl$_3$): δ 9.64 (d, J=3.0 Hz, 1H); 9.27 (d, J=6.0 Hz, 1H); 7.95 (d, J=2.5 Hz, 1H); 7.81 (dd, J=2.5 Hz, J=5.5 Hz, 1H); 6.79 (d, J=2.5 Hz, 1H).

Intermediate 4

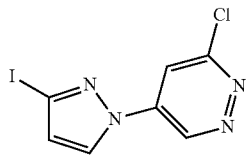

3-Chloro-5-(3-iodo-1H-pyrazol-1-yl)pyridazine

To a solution of 3-iodopyrazole (500 mg, 2.58 mmol) and 3,5-dichloropyridazine (384 mg, 2.58 mmol) in anhydrous DMF (5 mL) at room temperature was added potassium tert-butoxide (289 mg, 2.58 mmol) in one portion. It was heated at 100° C. for 1 h. It was cooled to room temperature, diluted with EtOAc (50 mL), washed with satd aq. NaHCO$_3$ (10 mL) and water (100 mL). The aqueous layer was separated and extracted with EtOAc (3×50 mL). The combined organic layers were washed with water (100 mL), brine (100 mL), dried over Na$_2$SO$_4$, filtered and concentrated. The residue was purified by flash chromatography (ISCO Combiflash, Gold 40 g, 0-60% EtOAc in hexanes) to give 3-chloro-5-(3-iodo-1H-pyrazol-1-yl)pyridazine, as a white solid. LCMS calc.=306.92. found=306.96 (M+H)$^+$. $^1$H NMR (500 MHz, CHCl$_3$-d): δ 9.54 (d, J=2.3 Hz, 1H); 7.94 (d, J=2.7 Hz, 1H); 7.90 (d, J=2.3 Hz, 1H); 6.81 (d, J=2.7 Hz, 1H).

Intermediate 5

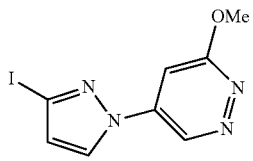 [SMILES: COc1cc(-n2ccc(I)n2)cnn1]

5-(3-Iodo-1H-pyrazol-1-yl)-3-methoxypyridazine

To a suspension of 3-chloro-5-(3-iodo-1H-pyrazol-1-yl)pyridazine (400 mg, 1.305 mmol) in MeOH (1 mL) was added triflic acid (300 μl, 3.38 mmol). The mixture was stirred at 50° C. for 6 h. It became a slight yellow solution. TEA (0.5 mL) was added and the mixture was concentrated and purified by flash chromatography (ISCO Combiflash, 40 g, 0-60% EtOAc in hexane) to give 5-(3-iodo-1H-pyrazol-1-yl)-3-methoxypyridazine. LCMS calc.=302.97. found=302.88 (M+H)$^+$.

Intermediate 6

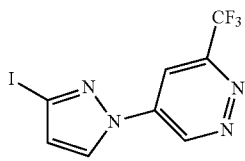 [SMILES: FC(F)(F)c1cc(-n2ccc(I)n2)cnn1]

5-(3-Iodo-1H-pyrazol-1-yl)-3-(trifluoromethyl)pyridazine

Step 6-1: 5-Chloro-3-iodopyridazine (Intermediate 6-1)

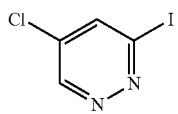

A solution of pyridine (0.72 mL, 8.90 mmol), 5-chloropyridazin-3(2H)-one (1 g, 7.66 mmol) in MeCN (7 mL) was cooled to 0° C. and trifluoromethanesulfonic anhydride (2.4 g, 8.51 mmol) was added dropwise over 2 min. It was stirred for 30 min at room temperature, then charged with sodium iodide (5.74 g, 38.3 mmol) in one portion. Triflic acid (0.75 mL, 8.45 mmol) was added dropwise and the mixture was stirred for 1 h. It was quenched with water (10 mL) and 10 M NaOH (~1.5 mL) and 1 M NaOH (3 mL) were added to adjust pH to 10. 10% Aqueous Na$_2$CO$_3$ (10 mL), and saturated aqueous sodium thiosulfate (30 mL) were added and the mixture was extracted with EtOAc (2×50 mL). The combined organic layers were washed with brine, dried over Na$_2$SO$_4$, filtered and concentrated. The residue was purified twice by flash chromatography (ISCO Combiflash, 40 g, 0-40% EtOAc in hexanes, then Gold 40 g, 0-40% EtOAc in hexanes) to give 5-chloro-3-iodopyridazine. LCMS calc.=240.90. found=240.92 (M+H)$^+$.

Step 6-2: 5-Chloro-3-(trifluoromethyl)pyridazine (Intermediate 6-2)

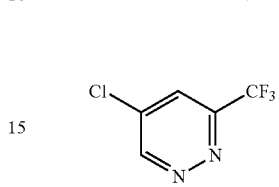

Cuprous iodide (0.77 g, 4.04 mmol) and potassium fluoride (0.24 g, 4.13 mmol) were thoroughly mixed and flame-heated under gentle shaking and at reduced pressure for 30 min until a greenish color appeared. 5-Chloro-3-iodopyridazine (0.88 g, 3.66 mmol), anhydrous DMF (2 mL), N-methyl-2-pyrrolidinone (2 mL) and (trifluoromethyl)trimethylsilane (0.57 g, 4.01 mmol) were added and the slurry was stirred vigorously for 16 h at room temperature. It was quenched with satd aq. NH$_4$Cl (20 mL) and EtOAc (20 mL). The mixture was filtered through Celite and separated. The aqueous layer was extracted with EtOAc (2×30 mL). The combined organic layers were filtered and washed with satd aq. NaHCO$_3$ and brine, dried over Na$_2$SO$_4$, filtered and concentrated. The residue was purified by flash chromatography (ISCO Combiflash, Gold 40 g, 0-30% EtOAc in hexanes) to give 5-chloro-3-(trifluoromethyl)pyridazine as the desired product. $^1$H NMR (500 MHz, CDCl$_3$): δ 9.41 (d, J=2.3 Hz, 1H); 7.90 (d, J=2.3 Hz, 1H).

Step 6-3: 5-(3-Iodo-1H-pyrazol-1-yl)-3-(trifluoromethyl)pyridazine

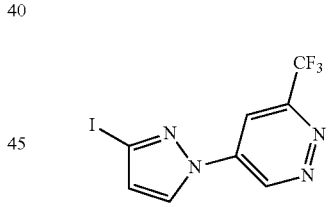

To 3-iodopyrazole (124 mg, 0.641 mmol) in DMF (2 mL) was added potassium tert-butoxide (53 mg, 0.472 mmol) at 0° C. The mixture was stirred at room temperature for 15 min. It was transferred into a solution of 5-chloro-3-(trifluoromethyl)pyridazine (78 mg, 0.427 mmol) in DMF (2 mL) at 0° C. It was warmed to room temperature, stirring for 30 min. It was diluted with EtOAc (20 mL), washed with water (3×20 mL), the combined aqueous layers were extracted with EtOAc (30 mL), the combined organic layers were washed with brine (30 mL), dried over Na$_2$SO$_4$, filtered and concentrated. The residue was purified by flash chromatography (ISCO Combiflash, 12 g, 0-100% EtOAc in hexanes) to give a mixture of 3-iodopyrazole and the desired product (1:2, 180 mg). It was dissolved in anhydrous CH$_2$Cl$_2$ (2 mL) and added a little bit of DMAP and of di-tert-butyl dicarbonate (~100 mg). It was stirred at room temperature for 10 min and purified by flash chromatography (ISCO Combiflash, 0-40% EtOAc in hexanes) to give 5-(3-iodo-1H-pyrazol-1-yl)-3-(trifluoromethyl)pyridazine, as white solid. LCMS calc.=340.95. found=340.84 (M+H)$^+$.

¹H NMR (500 MHz, CHCl₃-d): δ 9.78 (d, J=2.5 Hz, 1H); 8.17 (d, J=2.5 Hz, 1H); 8.04 (d, J=2.7 Hz, 1H); 6.84 (d, J=2.7 Hz, 1H).

Intermediate 7

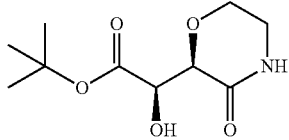 [SMILES: CC(C)(C)OC(=O)[C@H](O)[C@H]1OCCNC1=O]

(R)-tert-Butyl 2-hydroxy-2-((R)-3-oxomorpholin-2-yl)acetate

This compound was synthesized as in WO2010065717.

Intermediate 8

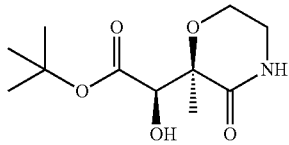

(R)-tert-Butyl 2-hydroxy-2-((R)-2-methyl-3-oxomorpholin-2-yl)acetate Step 8-1: (R)-tert-Butyl 2-hydroxy-2-((R)-4-(4-methoxybenzyl)-3-oxomorpholin-2-yl)acetate (Intermediate 8-1)

To (R)-tert-butyl 2-hydroxy-2-((R)-3-oxomorpholin-2-yl)acetate (10 g, 43.2 mmol) in DMF (108 mL) in a 1 L round bottom flask was added sodium hydride (1.730 g, 43.2 mmol) at 25° C. After stirring for 2 h, to the reaction vessel was added 4-methoxybenzyl chloride (5.87 mL, 43.2 mmol). The reaction was then stirred at 25° C. for 2 days. DMF was removed in vacuo. The residue was diluted with EtOAc, washed with sat. NH₄Cl(aq). The organic layer was dried over MgSO₄, filtered and concentrated. The crude product was loaded on ISCO silica gel column eluting with 0-30%-50% EtOAc in hexanes to afford (R)-tert-butyl 2-hydroxy-2-((R)-4-(4-methoxybenzyl)-3-oxomorpholin-2-yl)acetate. LCMS calc.=374.16. found=373.95 (M+Na)⁺.

Step 8-2: (R)-tert-Butyl 2-hydroxy-2-((R)-4-(4-methoxybenzyl)-2-methyl-3-oxomorpholin-2-yl)acetate (Intermediate 8-2)

To (R)-tert-butyl 2-hydroxy-2-((R)-4-(4-methoxybenzyl)-3-oxomorpholin-2-yl)acetate in THF (42.7 mL) cooled to −78° C. was added 1.8 M LDA (11.86 mL, 21.34 mmol) in THF. The reaction was stirred at −78° C. for 2 h. Methyl iodide (0.641 mL, 10.24 mmol) was then added slowly to the reaction at −78° C. and the reaction was stirred at the same temperature for 1 h. The reaction was then slowly warmed to 25° C. and stirred overnight. To the reaction was added saturated bicarbonate (aq). The aqueous layer was extracted with EtOAc (3×). The combined organic layers were washed with saturated bicarbonate (aq) and then brine, dried over MgSO₄, filtered and the filtrate concentrated. The crude product was purified by ISCO (0-30-50% EtOAc in hexanes) to afford (R)-tert-Butyl 2-hydroxy-2-((R)-4-(4-methoxybenzyl)-2-methyl-3-oxomorpholin-2-yl)acetate. LCMS calc.=309.12. found=309.92 (M+H—C₄H₉)⁺.

Step 8-3: (R)-tert-Butyl 2-hydroxy-2-((R)-2-methyl-3-oxomorpholin-2-yl)acetate

To a solution of (R)-tert-butyl 2-hydroxy-2-((R)-4-(4-methoxybenzyl)-2-methyl-3-oxomorpholin-2-yl)acetate (860 mg, 2.353 mmol) in MeCN (42.4 mL) and water (4.71 mL) was added ceric ammonium nitrate (2.58 g, 4.71 mmol) at 0° C. The reaction was warmed to 25° C. and stirred overnight. To the reaction was added ceric ammonium nitrate (2.58 g, 4.71 mmol) and the reaction was stirred at 25° C. for another 12 h. To the reaction was added saturated bicarbonate (aq) until the pH of the reaction mixture reached 4.5 to 5. The resulting suspension was filtered over Celite and the filter cake was washed with CH₂Cl₂, then with 5% MeOH in CH₂Cl₂. The combined organic phases were washed with brine, dried over MgSO₄, filtered and concentrated. The crude product was purified by ISCO (40 g silica gel column, 0-50-100% then 100% EtOAc in hexanes) to afford (R)-tert-butyl 2-hydroxy-2-((R)-2-methyl-3-oxomorpholin-2-yl)acetate, as a white solid. ¹H NMR (500 MHz, CDCl₃): δ 5.98, (s, 1H); 4.30 (d, J=8.6 Hz, 1H); 4.01 (d, J=12.0 Hz, 1H); 3.95-3.88 (m, 2H); 3.61-3.54 (m, 1H); 3.30 (dd, J=11.8, 4.0 Hz, 1H); 1.60 (s, 3H); 1.54 (s, 9H).

Intermediate 9 and 10

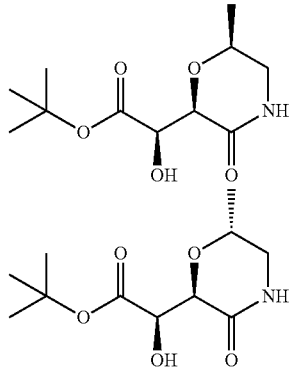

(R)-tert-Butyl 2-hydroxy-2-((2R,6S)-6-methyl-3-oxomorpholin-2-yl)acetate and (R)-tert-Butyl 2-hydroxy-2-((2R,6R)-6-methyl-3-oxomorpholin-2-yl)acetate Step 9-1: 1-((4-Methoxybenzyl)amino)propan-2-ol (Intermediate 9-1)

1-Amino-2-propanol (1.00 mL, 13.31 mmol) was added to a stirred solution of p-anisaldehyde (1.70 mL, 13.98 mmol) in absolute EtOH (18.0 mL) at 25° C. and the reaction mixture was stirred overnight. The reaction mixture was cooled to 0° C., sodium borohydride (0.756 g, 19.97 mmol) was added and the reaction mixture was warmed to room temperature and stirred for 7 h. The reaction mixture was diluted with EtOAc and water and the organic layer was separated, washed with brine, dried (Na₂SO₄) and concentrated in vacuo to give the crude product. This was purified by flash chromatography (Isco Combiflash Rf, RediSep Silica 80 g, 60 mL/min, loaded using solid loading cartridge after dissolving in CH₂Cl₂, 100% CH₂Cl₂ for 2 min, gradient to 10% (2M NH₃ in MeOH) in CH₂Cl₂ over 25 min, isocratic at 10% (2M NH$_3$ in MeOH) in CH$_2$Cl$_2$ for 23 min) to afford 1-((4-methoxybenzyl)amino)propan-2-ol, as a colorless oil. LCMS calc.=196.13. found=196.21 (M+H)$^+$. $^1$H NMR (600 MHz, CH$_3$CN-d$_3$): δ 7.23 (d, J=8.3 Hz, 2H); 6.86 (d, J=8.5 Hz, 2H); 3.75 (s, 3H); 3.71-3.62 (m, 3H); 2.54 (dd, J=11.9, 3.7 Hz, 1H); 2.35 (dd, J=11.9, 8.5 Hz, 1H); 1.94-1.91 (m, 1H); 1.04 (d, J=6.2 Hz, 3H).

Step 9-2: 2-Chloro-N-(4-methoxybenzyl)propan-1-amine (Intermediate 9-2)

Thionyl chloride (1.72 mL, 23.63 mmol) was added to a stirred solution of 1-((4-methoxybenzyl)amino)propan-2-ol (2.3072 g, 11.82 mmol) in dry 1,2-dichloroethane (59.1 mL) and the resulting solution was heated at 60° C. for 4 h. After this time the mixture was concentrated in vacuo to give the crude product as an HCl salt. This was partitioned between MTBE and satd aq. NaHCO$_3$. The aqueous layer was extracted with MTBE (2×). The combined organic layers were dried (Na$_2$SO$_4$) and concentrated in vacuo to give crude 2-chloro-N-(4-methoxybenzyl)propan-1-amine, as a free base. This was used in the next step without any further purification. LCMS calc.=214.10. found=214.17 (M+H)$^+$. $^1$H NMR (600 MHz, CH$_3$CN-d$_3$): δ 7.55 (d, J=8.4 Hz, 2H); 6.95 (d, J=8.5 Hz, 2H); 4.65-4.58 (m, 1H); 4.21-4.02 (m, 3H); 3.80 (s, 3H); 3.23-3.16 (m, 1H); 3.05-2.98 (m, 1H); 1.52 (d, J=6.7 Hz, 3H).

Step 9-3: (2R,3R)-2,3-Diacetoxy-4-((2-chloropropyl)(4-methoxybenzyl)amino)-4-oxobutanoic acid (Intermediate 9-3)

A solution of 2-chloro-N-(4-methoxybenzyl)propan-1-amine (2.53 g, 11.84 mmol) in dry THF (59.2 mL) was added a to stirred solution of (+)-diacetyl-L-tartaric anhydride (2.61 g, 12.08 mmol) in dry THF (59.2 mL) at 0° C. under N$_2$ and the reaction was stirred at 4° C. overnight (reaction was transferred to refrigerator for overnight portion, no stirring). The reaction was concentrated in vacuo to afford crude (2R,3R)-2,3-diacetoxy-4-((2-chloropropyl)(4-methoxybenzyl)amino)-4-oxobutanoic acid which was carried forward without any further purification. LCMS calc.=430.13. found=430.06 (M+H)$^+$.

Step 9-4: (2R,3R)-1-(tert-Butoxy)-4-((2-chloropropyl)(4-methoxybenzyl)amino)-1,4-dioxobutane-2,3-diyl diacetate (Intermediate 9-4)

2-tert-Butyl-1,3-diisopropylisourea (8.73 mL, 37.3 mmol) was added to a stirred solution of (2R,3R)-2,3-diacetoxy-4-((2-chloropropyl)(4-methoxybenzyl)amino)-4-oxobutanoic acid (5.09 g, 11.84 mmol) in dry THF (118 mL) and the mixture was heated at 60° C. under a reflux condenser under N$_2$. After 4 h another 1.05 eq of 2-tert-butyl-1,3-diisopropylisourea was added and the reaction was heated at 60° C. for 1 h. The reaction mixture was concentrated in vacuo to give the crude product. This was purified by flash chromatography (Isco Combiflash Rf, RediSep Silica 80 g, 60 mL/min, loaded using solid loading cartridge after dissolving in CH$_2$Cl$_2$, 100% hexanes for 3 min, gradient to 50% EtOAc in hexanes over 24 min, isocratic at 50% EtOAc in hexanes for 23 min) to afford (2R,3R)-1-(tert-butoxy)-4-(2-chloropropyl)(4-methoxybenzyl)amino)-1,4-dioxobutane-2,3-diyl diacetate, as a colorless oil. LCMS calc.=486.19. found=486.18 (M+H)$^+$.

Step 9-5: (2R,3R)-tert-Butyl 4-((2-chloropropyl)(4-methoxybenzyl)amino)-2,3-dihydroxy-4-oxobutanoate (Intermediate 9-5)

Potassium cyanide (0.293 g, 4.49 mmol) was added to a stirred solution of (2R,3R)-1-(tert-butoxy)-4-((2-chloropropyl)(4-methoxybenzyl)amino)-1,4-dioxobutane-2,3-diyl diacetate (4.20 g, 8.64 mmol) in MeOH (86 mL) at 0° C. under N$_2$. The resulting mixture was stirred at 0° C. for 4 h. The reaction mixture was diluted with water and extracted with MTBE (3×). The combined extracts were dried (Na$_2$SO$_4$) and concentrated in vacuo to afford (2R,3R)-tert-butyl 4-((2-chloropropyl)(4-methoxybenzyl)amino)-2,3-dihydroxy-4-oxobutanoate, as a colorless oil. This was carried forward with no further purification. LCMS calc.=402.17. found=402.17 (M+H)$^+$.

Step 9-6: (R)-tert-Butyl 2-hydroxy-2-((2R,6S)-4-(4-methoxybenzyl)-6-methyl-3-oxomorpholin-2-yl)acetate (Intermediate 9-6) and (R)-tert-Butyl 2-hydroxy-2-((2R,6R)-4-(4-methoxybenzyl)-6-methyl-3-oxomorpholin-2-yl)acetate (Intermediate 9-7)

Benzyltrimethylammonium hydroxide (40 wt % in MeOH) (9.50 mL, 20.90 mmol) was added to a stirred mixture of (2R,3R)-tert-butyl 4-((2-chloropropyl)(4-methoxybenzyl)amino)-2,3-dihydroxy-4-oxobutanoate (4.20 g, 10.45 mmol), CH$_2$Cl$_2$ (85 mL) and water (19.7 mL) at 25° C. and the mixture was stirred for 4 h. The mixture was diluted with water and extracted with CH$_2$Cl$_2$ (3×). The combined extracts were dried (Na$_2$SO$_4$) and concentrated in vacuo to give the crude product. This was purified by flash chromatography (Isco Combiflash Rf, Gold RediSep Silica 80 g, 60 mL/min, loaded using solid loading cartridge after dissolving in CH$_2$Cl$_2$, 100% toluene for 3 min, gradient to 50% EtOAc in toluene over 42 min, isocratic at 50% EtOAc in toluene for 5 min) to afford a mixture of desired product diastereoisomers. This was purified by chiral SFC (AS, 20×250 mm, 20% 2:1 MeOH: MeCN/CO$_2$, 35° C.) to afford the two diastereoisomers in order of elution (R)-tert-butyl 2-hydroxy-2-((2R,6S)-4-(4-methoxybenzyl)-6-methyl-3-oxomorpholin-2-yl)acetate and (R)-tert-butyl 2-hydroxy-2-((2R,6R)-4-(4-methoxybenzyl)-6-methyl-3-oxomorpholin-2-yl)acetate, as colorless solids. Diastereoisomer 1: LCMS calc.=366.19. found=366.20 (M+H)$^+$. $^1$H NMR (600 MHz, CHCl$_3$-d): δ 7.20 (d, J=8.4 Hz, 2H); 6.84 (d, J=8.5 Hz, 2H); 4.71 (s, 1H); 4.62 (d, J=14.6 Hz, 1H); 4.52 (d, J=2.1 Hz, 1H); 4.47 (d, J=14.6 Hz, 1H); 3.88-3.84 (m, 1H); 3.78 (s, 3H); 3.15 (t, J=11.3 Hz, 1H); 2.98-2.91 (m, 1H); 1.48 (s, 9H); 1.14 (d, J=6.2 Hz, 3H). Diastereoisomer 2: LCMS calc.=366.19. found=366.20 (M+H)$^+$. $^1$H NMR (600 MHz, CHCl$_3$-d): δ 7.20 (d, J=8.4 Hz, 2H); 6.85 (d, J=8.5 Hz, 2H); 4.81 (d, J=2.3 Hz, 1H); 4.65 (d, J=14.6 Hz, 1H); 4.60 (d, J=2.4 Hz, 1H); 4.51 (d, J=14.7 Hz, 1H); 4.49-4.45 (m, 1H); 3.78 (s, 3H); 3.19-3.09 (m, 1H); 3.05 (dd, J=12.3, 8.7 Hz, 1H); 1.49 (s, 9H); 1.07 (d, J=6.3 Hz, 3H).

Step 9-7: (R)-tert-Butyl 2-hydroxy-2-((2R,6S)-6-methyl-3-oxomorpholin-2-yl)acetate Ceric ammonium nitrate (2.272 g, 4.14 mmol) was added to a stirred solution of (R)-tert-butyl 2-hydroxy-2-((2R,6S)-4-(4-methoxybenzyl)-6-methyl-3-oxomorpholin-2-yl)acetate (0.3786 g, 1.036 mmol) in MeCN (13.3 mL) and water (1.5 mL) at 0° C. The reaction was warmed to room temperature and stirred for 5 h. The reaction was diluted with satd aq. NaHCO$_3$ and the resulting precipitate was collected by filtration and washed with CH$_2$Cl$_2$. The organic layer of the filtrate was separated and the aqueous layer was further extracted with CH$_2$Cl$_2$ (2×). The combined organic extracts were dried (Na$_2$SO$_4$) and concentrated in vacuo to give the crude product. This was left on the high vacuum pump for 3 days during which time the 4-MeO-benzaldehyde byproduct was removed to afford the desired product (R)-tert-butyl 2-hydroxy-2-((2R,6S)-6-methyl-3-oxomorpholin-2-yl)acetate, as a colorless solid. LCMS calc.=246.13. found=246.20 (M+H)$^+$. $^1$H NMR (500 MHz, CHCl$_3$-d): δ 7.20 (s, 1H); 4.64 (d, J=7.6 Hz, 1H); 4.48 (d, J=2.1 Hz, 1H); 3.98-3.83 (m, 1H); 3.41 (d, J=12.2 Hz, 1H); 3.33-3.15 (m, 2H); 1.50 (s, 9H); 1.23 (d, J=6.2 Hz, 3H).

Step 9-8: (R)-tert-Butyl 2-hydroxy-2-((2R,6R)-6-methyl-3-oxomorpholin-2-yl)acetate Ceric ammonium nitrate (1.479 g, 2.70 mmol) was added to a stirred solution of (R)-tert-butyl 2-hydroxy-2-((2R,6R)-4-(4-methoxybenzyl)-6-methyl-3-oxomorpholin-2-yl)acetate (0.2465 g, 0.675 mmol) in MeCN (8.7 mL) and water (0.96 mL) at 0° C. The reaction was warmed to room temperature and stirred for 5 h. The reaction was diluted with satd aq. NaHCO$_3$ and the resulting precipitate was collected by filtration and washed with CH$_2$Cl$_2$. The organic layer of the filtrate was separated and the aqueous layer was further extracted with CH$_2$Cl$_2$ (2×). The combined organic extracts were dried (Na$_2$SO$_4$) and concentrated in vacuo to give the crude product. This was left on the high vacuum pump for 3 days during which time the 4-MeO-benzaldehyde byproduct was removed to afford the desired product (R)-tert-butyl 2-hydroxy-2-((2R,6R)-6-methyl-3-oxomorpholin-2-yl)acetate, as a colorless solid. LCMS calc.=246.13. found=246.20 (M+H)$^+$. $^1$H NMR (500 MHz, CHCl$_3$-d): δ 7.45 (s, 1H); 4.72 (s, 1H); 4.56 (d, J=2.3 Hz, 1H); 4.49 (d, J=9.8 Hz, 1H); 3.55 (s, 1H); 3.39-3.32 (m, 1H); 3.22-3.04 (m, 1H); 1.51 (s, 9H); 1.18 (d, J=6.3 Hz, 3H).

Intermediate 11

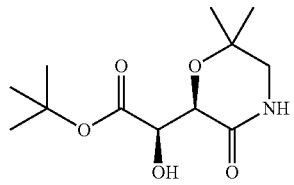 [SMILES: CC(C)(C)OC(=O)[C@H](O)[C@H]1OC(C)(C)CNC1=O]

(R)-tert-Butyl 2-((R)-6,6-dimethyl-3-oxomorpholin-2-yl)-2-hydroxyacetate

Step 11-1: N-(4-Methoxybenzyl)-2-methylprop-2-en-1-amine (Intermediate 11-1)

2-Methylallylamine (1.28 mL, 14.06 mmol) was added to a stirred solution of p-anisaldehyde (1.71 mL, 14.06 mmol) in absolute EtOH (19.1 mL) at 25° C. and the reaction mixture was stirred overnight. The reaction mixture was cooled to 0° C., sodium borohydride (0.798 g, 21.09 mmol) was added and the reaction mixture was warmed to room temperature and stirred for 7 h. The reaction mixture was diluted with EtOAc and water and the organic layer was separated, washed with brine, dried (Na$_2$SO$_4$) and concentrated in vacuo to give the crude product. This was purified by flash chromatography (Isco Combiflash Rf, RediSep Silica 80 g, 60 mL/min, loaded using solid loading cartridge after dissolving in CH$_2$Cl$_2$, 100% CH$_2$Cl$_2$ for 2 min, gradient to 10% (2M NH$_3$ in MeOH) in CH$_2$Cl$_2$ over 25 min, isocratic at 10% (2M NH$_3$ in MeOH) in CH$_2$Cl$_2$ for 23 min) to afford N-(4-methoxybenzyl)-2-methylprop-2-en-1-amine, as a colorless oil. LCMS calc.=192.14. found=192.22 (M+H)$^+$. $^1$H NMR (500 MHz, CHCl$_3$-d): δ 6.75 (d, J=8.3 Hz, 2H); 6.37 (d, J=8.4 Hz, 2H); 4.40 (s, 1H); 4.36 (s, 1H); 3.30 (s, 3H); 3.20 (s, 2H); 2.69 (s, 2H); 1.27 (s, 3H).

Step 11-2: (2R,3R)-2,3-Diacetoxy-4-((4-methoxybenzyl)(2-methylallyl)amino-4-oxobutanoic acid (Intermediate 11-2)

A solution of N-(4-methoxybenzyl)-2-methylprop-2-en-1-amine (2.26 g, 11.82 mmol) in dry THF (59.1 mL) was added a to stirred solution of (+)-diacetyl-1-tartaric anhydride (2.61 g, 12.05 mmol) in dry THF (59.1 mL) at 0° C. under N$_2$ and the reaction was stirred at 4° C. overnight (reaction was transferred to refrigerator for overnight portion, no stirring). The reaction was concentrated in vacuo to afford (2R,3R)-2,3-diacetoxy-4-((4-methoxybenzyl)(2-methylallyl)amino)-4-oxobutanoic acid which was carried forward without any further purification. LCMS calc.=408.17. found=408.14 (M+H)$^+$.

Step 11-3: (2R,3R)-1-Methoxy-4-((4-methoxybenzyl(2-methylallyl)amino-1,4-dioxobutane-2,3-diyl diacetate (Intermediate 11-3)

(Trimethylsilyl)diazomethane (2M in Et$_2$O) (1.96 mL, 3.93 mmol) was added to a stirred solution of (2R,3R)-2,3-diacetoxy-4-((4-methoxybenzyl)(2-methylallyl)amino)-4-oxobutanoic acid (1.00 g, 2.455 mmol) in MeOH (2.5 mL) and CH$_2$Cl$_2$ (22.1 mL) at room temperature and the resulting solution was stirred for 1 h. After this time the reaction mixture was concentrated in vacuo to afford the crude methyl ester. This was purified by flash chromatography (Isco Combiflash Rf, RediSep Silica 40 g, 40 mL/min, loaded using solid loading cartridge after dissolving in CH$_2$Cl$_2$, 100% hexanes for 2 min, gradient to 50% EtOAc in hexanes over 13 min, isocratic at 50% EtOAc in hexanes for 15 min) to afford (2R,3R)-1-methoxy-4-((4-methoxybenzyl)(2-methylallyl)amino)-1,4-dioxobutane-2,3-diyl diacetate, as a colorless oil. LCMS calc.=422.18. found=422.16 (M+H)$^+$.

Step 11-4: (2R,3R)-Methyl 2,3-dihydroxy-4-((4-methoxybenzyl)(2-methylallyl)amino)-4-oxobutanoate (Intermediate 11-4)

Potassium cyanide (0.076 g, 1.172 mmol) was added to a stirred solution of (2R,3R)-1-methoxy-4-(4-methoxybenzyl)(2-methylallyl)amino)-1,4-dioxobutane-2,3-diyl diacetate (0.95 g, 2.254 mmol) in MeOH (22.5 mL) at 0° C. under N$_2$. The resulting mixture was stirred at 0° C. for 4 h. Solid NaHCO$_3$ (0.197 g, 2.344 mmol) was added and the reaction mixture was diluted with water and extracted with MTBE (3×). The combined extracts were dried (Na$_2$SO$_4$) and concentrated in vacuo to afford (2R,3R)-methyl 2,3-dihydroxy-4-((4-methoxybenzyl)(2-methylallyl)amino)-4-oxobutanoate, as a colorless oil. This was carried forward with no further purification. LCMS calc.=338.16. found=338.18 (M+H)$^+$.

Step 11-5: (R)-Methyl 2-hydroxy-2-((R)-4-(4-methoxybenzyl)-6,6-dimethyl-3-oxomorpholin-2-yl)acetate (Intermediate 11-5)

Mercuric acetate (0.670 g, 2.101 mmol) was added to solution of (2R,3R)-methyl 2,3-dihydroxy-4-((4-methoxybenzyl)(2-methylallyl)amino)-4-oxobutanoate (0.4726 g, 1.401 mmol) in water (7.0 mL) and THF (7.0 mL) at 25° C. and the reaction was stirred for 3 days. After this time sodium borohydride (0.085 g, 2.241 mmol) was added and the reaction was stirred at 25° C. overnight. After this time another 1.6 eq sodium borohydride was added and the reaction was stirred for 6 h. The reaction was diluted with water and extracted with MTBE (3×). The combined extracts were dried (Na$_2$SO$_4$) and concentrated in vacuo to give the crude product. This was purified by flash chromatography (Isco Combiflash Rf, RediSep Silica 40 g, 40 mL/min, loaded using solid loading cartridge after dissolving in CH$_2$Cl$_2$, 100% hexanes for 2 min, gradient to 100% EtOAc over 22 min, isocratic at 100% EtOAc for 6 min) to afford (R)-methyl 2-hydroxy-2-((R)-4-(4-methoxybenzyl)-6,6-dimethyl-3-oxomorpholin-2-yl)acetate, as a colorless oil. LCMS calc.=338.16. found=338.13 (M+H)$^+$. $^1$H NMR (600 MHz, CHCl$_3$-d): δ 7.19 (d, J=8.4 Hz, 2H); 6.84 (d, J=8.4 Hz, 2H); 4.77 (s, 1H); 4.67 (d, J=14.5 Hz, 1H); 4.49 (d, J=2.2 Hz, 1H); 4.42 (d, J=14.5 Hz, 1H); 3.77 (s, 6H); 3.29 (d, J=12.2 Hz, 1H); 2.78 (d, J=12.2 Hz, 1H); 1.16 (s, 6H).

Step 11-6: (R)-2-Hydroxy-2-((R)-4-(4-methoxybenzyl)-6,6-dimethyl-3-oxomorpholin-2-yl)acetic acid (Intermediate 11-6)

1N Lithium hydroxide (578 μL, 0.578 mmol) was added to a stirred solution of (R)-methyl 2-hydroxy-2-((R)-4-(4-methoxybenzyl)-6,6-dimethyl-3-oxomorpholin-2-yl)acetate (97.5 mg, 0.289 mmol) in 1,4-dioxane (5.4 mL) and water (1.3 mL) and the mixture was stirred at 25° C. for 2 h. The reaction was acidified with 1N aq. HCl (1.0 mL) then extracted with MTBE (3×). The combined extracts were dried (Na$_2$SO$_4$) and concentrated in vacuo to afford (R)-2-hydroxy-2-((R)-4-(4-methoxybenzyl)-6,6-dimethyl-3-oxomorpholin-2-yl)acetic acid, as a colorless solid. LCMS calc.=324.14. found=324.13 (M+H)$^+$. $^1$H NMR (500 MHz, CHCl$_3$-d): δ 7.19 (d, J=8.3 Hz, 2H); 6.85 (d, J=8.4 Hz, 2H); 5.12 (s, 1H); 4.84 (d, J=2.2 Hz, 1H); 4.71 (d, J=14.4 Hz, 1H); 4.61 (d, J=2.2 Hz, 1H); 4.39 (d, J=14.5 Hz, 1H); 3.78 (s, 3H); 3.33 (d, J=12.3 Hz, 1H); 2.81 (d, J=12.3 Hz, 1H); 1.18 (s, 3H).

Step 11-7: (R)-tert-Butyl 2-hydroxy-2-((R)-4-(4-methoxybenzyl)-6,6-dimethyl-3-oxomorpholin-2-yl) acetate (Intermediate 11-7)

2-tert-Butyl-1,3-diisopropylisourea (222 μL, 0.950 mmol) was added to a stirred solution of (R)-2-hydroxy-2-((R)-4-(4-methoxybenzyl)-6,6-dimethyl-3-oxomorpholin-2-yl)acetic acid (102.4 mg, 0.317 mmol) in dry THF (921 μL) and the mixture was heated at 60° C. in a sealed vial under N$_2$. After 4 h the reaction mixture was diluted with MTBE and cooled with an ice bath. The urea precipitate was collected by filtration and the filtrate was concentrated in vacuo to give the crude product. This was purified by flash chromatography (Isco Combiflash Rf, RediSep Silica 12 g, 30 mL/min, loaded as a solution in CH$_2$Cl$_2$, 100% hexanes for 1 min, gradient to 50% EtOAc in hexanes over 11 min, isocratic at 50% EtOAc in hexanes for 4 min) to afford (R)-tert-butyl 2-hydroxy-2-((R)-4-(4-methoxybenzyl)-6,6-dimethyl-3-oxomorpholin-2-yl)acetate, as a colorless oil. LCMS calc.=380.21. found=380.15 (M+H)$^+$. $^1$H NMR (600 MHz, CHCl$_3$-d): δ 7.20 (d, J=8.4 Hz, 2H); 6.84 (d, J=8.5 Hz, 2H); 4.72 (d, J=14.5 Hz, 1H); 4.67 (d, J=6.7 Hz, 1H); 4.48 (d, J=2.1 Hz, 1H); 4.37 (d, J=14.5 Hz, 1H); 3.77 (s, 3H); 3.29 (d, J=12.1 Hz, 1H); 3.24 (d, J=8.1 Hz, 1H); 2.78 (d, J=12.1 Hz, 1H); 1.46 (s, 9H); 1.14 (s, 6H).

Step 11-8: (R)-tert-Butyl 2-((R)-6,6-dimethyl-3-oxomorpholin-2-yl)-2-hydroxyacetate (INTERMEDIATE 11)

Ceric ammonium nitrate (556 mg, 1.014 mmol) was added to a stirred solution of (R)-tert-butyl 2-hydroxy-2-((R)-4-(4-methoxybenzyl)-6,6-dimethyl-3-oxomorpholin-2-yl)acetate (96.2 mg, 0.254 mmol) in MeCN (3.3 mL) and water (0.36 mL) at 0° C. The reaction was warmed to room temperature and stirred for 5 h. The reaction was diluted with satd aq. NaHCO$_3$ and the resulting precipitate was collected by filtration and washed with CH$_2$Cl$_2$. The organic layer of the filtrate was separated and the aqueous layer was further extracted with CH$_2$Cl$_2$ (2×). The combined organic extracts were dried (Na$_2$SO$_4$) and concentrated in vacuo to give the crude product. This was left on the high vacuum pump for 3 days during which time the 4-MeO-benzaldehyde byproduct was removed to afford (R)-tert-Butyl 2-((R)-6,6-dimethyl-3-oxomorpholin-2-yl)-2-hydroxyacetate, as a colorless solid. LCMS calc.=260.15. found=260.20 (M+H)$^+$. $^1$H NMR (500 MHz, CHCl$_3$-d): δ 7.28 (s, 1H); 4.59 (d, J=7.5 Hz, 1H); 4.41 (d, J=5.8 Hz, 1H); 3.44-3.35 (m, 2H); 3.01 (dd, J=12.1, 5.1 Hz, 1H); 1.46 (s, 9H); 1.32 (s, 3H); 1.22 (s, 3H).

Example 5

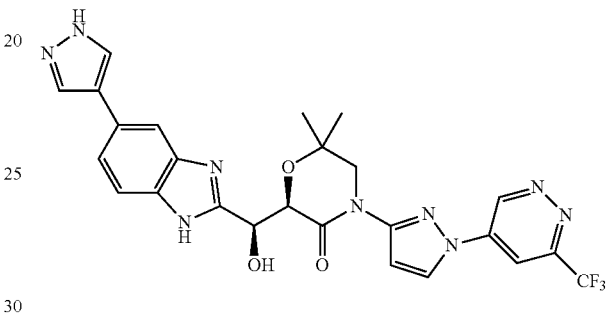

(R)-2-((S)-(5-(1H-Pyrazol-4-yl)-1H-benzo[d]imidazol-2-yl)(hydroxy)methyl)-6,6-dimethyl-4-(1-(6-(trifluoromethyl)pyridazin-4-yl)-1H-pyrazol-3-yl)morpholin-3-one Step 5-1: (R)-tert-Butyl 2-((R)-6,6-dimethyl-3-oxo-4-(1-(6-(trifluoromethyl)pyridazin-4-yl)-1H-pyrazol-3-yl)morpholin-2-yl)-2-hydroxyacetate (compound 5-1)

(R)-tert-Butyl 2-((R)-6,6-dimethyl-3-oxomorpholin-2-yl)-2-hydroxyacetate (250 mg, 0.964 mmol), 5-(3-iodo-1H-pyrazol-1-yl)-3-(trifluoromethyl)pyridazine (328 mg, 0.964 mmol), potassium phosphate (0.487 mL, 2.410 mmol), trans-N,N-dimethylcyclohexane-1,2-diamine (0.076 mL, 0.482 mmol), copper(I) iodide (92 mg, 0.482 mmol) and 1,4-dioxane (7 mL) were sealed in a reaction vessel. N$_2$ was bubbled through the mixture for 2 min then the vessel was sealed and heated at 80° C. for 4 h. The reaction crude was filtered into a stirred satd aq. NH$_4$Cl/ice mixture. The resulting mixture was partitioned between satd aq. NH$_4$Cl and EtOAc. The combined extracts were dried over Na$_2$SO$_4$, filtered and evaporated in vacuo. The pot residue was purified by flash chromatography (RediSep Column: Silica 120 g, EtOAc/hexanes) to afford (R)-tert-butyl 2-((R)-6,6-dimethyl-3-oxo-4-(1-(6-(trifluoromethyl)pyridazin-4-yl)-1H-pyrazol-3-yl)morpholin-2-yl)-2-hydroxyacetate, as a light yellow solid. LCMS calc.=472.18. found=471.91 (M+H)$^+$.

Step 5-2: (R)-2-((R)-6,6-Dimethyl-3-oxo-4-(1-(6-(trifluoromethyl)pyridazin-4-yl)-1H-pyrazol-3-yl)morpholin-2-yl)-2-hydroxyacetic acid hydrochloride (compound 5-2)

(R)-tert-Butyl 2-((R)-6,6-dimethyl-3-oxo-4-(1-(6-(trifluoromethyl)pyridazin-4-yl)-1H-pyrazol-3-yl)morpholin-2- yl)-2-hydroxyacetate (188.4 mg, 0.400 mmol), trifluoroacetic acid (0.5 mL, 0.400 mmol) and CH₂Cl₂ (8 mL) were stirred at room temperature for 2 h. Volatiles were removed under reduced pressure. The pot residue was stirred in hydrochloric acid (2 mL of a 4M solution in 1,4-dioxane, 8.00 mmol) at room temperature for 1 h. Volatiles were removed in vacuo. The resulting yellow oil was chased with toluene (5 mL×3) and evaporated in vacuo to afford (R)-2-((R)-6,6-dimethyl-3-oxo-4-(1-(6-(trifluoromethyl)pyridazin-4-yl)-1H-pyrazol-3-yl)morpholin-2-yl)-2-hydroxyacetic acid hydrochloride, as a yellow solid. LCMS (free acid) calc.=416.12. found=415.82 (M+H)⁺.

Step 5-3: (R)-2-((S)-Hydroxy(5-iodo-1H-benzo[d]imidazol-2-yl)methyl)-6,6-dimethyl-4-(1-(6-(trifluoromethyl)pyridazin-4-yl)-1H-pyrazol-3-yl)morpholin-3-one (compound 5-3)

(R)-2-((R)-6,6-Dimethyl-3-oxo-4-(1-(6-(trifluoromethyl)pyridazin-4-yl)-1H-pyrazol-3-yl)morpholin-2-yl)-2-hydroxyacetic acid hydrochloride (100 mg, 0.221 mmol), 4-iodo-1,2-benzenediamine (51.8 mg, 0.221 mmol), i-Pr₂NEt (0.116 mL, 0.664 mmol) and HATU (84 mg, 0.221 mmol) were stirred in DMF (2 mL) at room temperature for 2 h. To this mixture was added acetic acid (0.3 mL, 5.24 mmol). The reaction was heated in a 80° C. oil bath for 6 h then allowed to cool to ambient. The reaction crude was worked up with water/EtOAc. The combined extracts were dried over Na₂SO₄, filtered and evaporated in vacuo to afford a dark colored mixture. The pot residue was purified by preparative HPLC (reversed phase, YMC-Pack ODS C-18, 100×20 mm, MeCN/water (0% to 40% organic in 25 min, then to 100% in 5 min, 25 mL/min)) to afford (R)-2-((S)-hydroxy(5-iodo-1H-benzo[c/]imidazol-2-yl)methyl)-6,6-dimethyl-4-(1-(6-(trifluoromethyl)pyridazin-4-yl)-1H-pyrazol-3-yl)morpholin-3-one, as a brown solid. LCMS calc.=614.06. found=613.93 (M+H)⁺.

Step 5-4: (R)-2-((S)-(5-(1H-Pyrazol-4-yl)-1H-benzo[d]imidazol-2-yl)(hydroxy)methyl)-6,6-dimethyl-4-(1-(6-(trifluoromethyl)pyridazin-4-yl)-1H-pyrazol-3-yl)morpholin-3-one (EXAMPLE 5)

(R)-2-((S)-Hydroxy(5-iodo-1H-benzo[d]imidazol-2-yl)methyl)-6,6-dimethyl-4-(1-(6-(trifluoromethyl)pyridazin-4-yl)-1H-pyrazol-3-yl)morpholin-3-one (39 mg, 0.064 mmol), 1H-pyrazole-4-boronic acid (21.35 mg, 0.191 mmol), [1,1'-bis(diphenylphosphino)ferrocene]dichloropalladium (II) (9.31 mg, 0.013 mmol), cesium carbonate (62.2 mg, 0.191 mmol), DMA (0.5 mL) and water (0.063 mL) were mixed, degassed by purging with N₂ and placed in a 85° C. oil bath overnight. The crude was worked up with water/EtOAc. The combined extracts were dried over Na₂SO₄, filtered and evaporated in vacuo to afford a dark colored mixture. The resulting crude mixture was purified by preparative HPLC (reversed phase, YMC-Pack Pro C-18 100×20 mm, MeCN/water+0.05% formic acid (0% to 80% organic in 10 min, then to 100% for 2 min, 20 mL/min)) to afford (R)-2-((S)-(5-(1H-pyrazol-4-yl)-1H-benzo[d]imidazol-2-yl)(hydroxy)methyl)-6,6-dimethyl-4-(1-(6-(trifluoromethyl)pyridazin-4-yl)-1H-pyrazol-3-yl)morpholin-3-one, as a yellow glass. LCMS calc.=554.19. found=554.04 (M+H)⁺. ¹H NMR (500 MHz, CD₃OD): δ 9.96 (d, J=2.5 Hz, 1H); 8.67 (d, J=2.9 Hz, 1H); 8.41 (d, J=2.5 Hz, 1H); 7.94 (s, 2H); 7.72 (s, 1H); 7.58-7.52 (m, 1H); 7.48-7.45 (m, 1H); 7.40 (d, J=2.9 Hz, 1H); 5.59 (d, J=2.1 Hz, 1H); 4.87 (d, J=2.1 Hz, 1H); 4.24 (d, J=12.7 Hz, 1H); 3.96 (d, J=12.7 Hz, 1H); 1.40-1.35 (m, 6H).

Intermediate 12

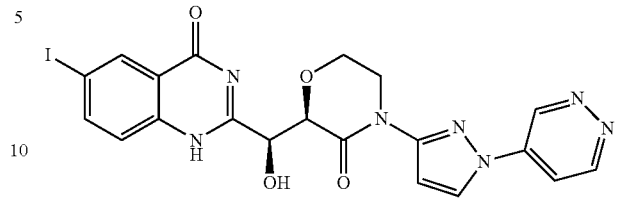

(R)-2-((S)-Hydroxy(6-iodo-4-oxo-1,4-dihydroquinazolin-2-yl)methyl)-4-(1-(pyridazin-4-yl)-1H-pyrazol-3-yl)morpholin-3-one Step 12-1: (3-Iodo-1H-pyrazol-1-yl)methyl pivalate (Intermediate 12-1)

3-Iodo-1H-pyrazole (19.44 g, 100 mmol) was charged to a flask followed by THF (237 mL) and the solution was cooled to −10° C. NaH (4.41 g, 110 mmol) was added in portions keeping the internal temperature below −10° C. The reaction was stirred for 30 min, then chloromethyl pivalate (17.45 mL, 120 mmol) was added and the reaction was stirred for 1 h at −10° C. and then allowed to warm to room temperature. The reaction was cooled in an ice bath and quenched with sat. NH₄Cl then diluted with EtOAc and water. The organic layer was washed with brine, dried over MgSO₄ and the solvent was removed. The product was purified by flash chromatography eluting with 0-50% EtOAc/hexane to give (3-iodo-1H-pyrazol-1-yl)methyl pivalate, as a white solid. LCMS calc.=309.01. found=308.87 (M+H⁺).

Step 12-2: (3-((R)-2-((R)-2-(tert-Butoxy)-1-hydroxy-2-oxoethyl)-3-oxomorpholino)-1H-pyrazol-1-yl)methyl pivalate (Intermediate 12-2)

(R)-tert-Butyl 2-hydroxy-2-((R)-3-oxomorpholin-2-yl)acetate (6.56 g, 21.29 mmol), (3-iodo-1H-pyrazol-1-yl)methyl pivalate (5.42 g, 23.42 mmol), potassium phosphate tribasic (9.04 g, 42.6 mmol) and 1,4-dioxane (65.6 mL) was charged to a vial and degassed for 5 min. Copper (I) iodide (4.05 g, 21.29 mmol) was added and the reaction was degassed for 20 min. trans-N,N-Dimethylcyclohexane-1,2-diamine (3.46 mL, 21.29 mmol) was then added and the reaction degassing was continued while heating to 85° C. (degassing stopped once internal temperature reached 50° C.). The reaction was stirred for 3 h. The reaction was cooled and filtered. The reaction was reverse quenched into 2N HCl (25 mL). The batch was filtered again, then the layers were separated. The organic phase was washed with NaHCO₃ and brine then dried over MgSO₄ and solvent was removed to give the crude product (5.3 g). The compound was purified by flash chromatography eluting with 0-60% EtOAc/hexane to give (3-((R)-2-((R)-2-(tert-butoxy)-1-hydroxy-2-oxoethyl)-3-oxomorpholino)-1H-pyrazol-1-yl)methyl pivalate, as a white solid. LCMS calc.=434.19. found=434.07 (M+Na⁺).

Step 12-3: (R)-2-Hydroxy-2-((R)-3-oxo-4-(1-((pivaloyloxy)methyl)-1H-pyrazol-3-yl)morpholin-2-yl) acetic acid (Intermediate 12-3)

(3-((R)-2-((R)-2-(tert-Butoxy)-1-hydroxy-2-oxoethyl)-3-oxomorpholino)-1H-pyrazol-1-yl)methyl pivalate (4 g, 9.72 mmol) was charged to a flask and dissolved in TFA (20 mL).

After 45 min dichloroethane was added and the solvent removed (2×50 mL). The batch was crystallized from EtOAc/heptane to give (R)-2-hydroxy-2-((R)-3-oxo-4-(1-((pivaloyloxy)methyl)-1H-pyrazol-3-yl)morpholin-2-yl) acetic acid, as a white solid. LCMS calc.=378.13. found=378.08 (M+Na$^+$).

Step 12-4: (3-((R)-2-((R)-2-((2-Carbamoyl-4-iodophenyl)amino)-1-hydroxy-2-oxoethyl)-3-oxomorpholino)-1H-pyrazol-1-yl)methyl pivalate (Intermediate 12-4)

(R)-2-Hydroxy-2-((R)-3-oxo-4-(1-((pivaloyloxy) methyl)-1H-pyrazol-3-yl)morpholin-2-yl)acetic acid (5 g, 14.07 mmol), 2-amino-5-iodobenzamide (3.80 g, 14.07 mmol), HATU (5.35 g, 14.07 mmol), and 1-hydroxy-7-azabenzotriazole (1.915 g, 14.07 mmol) were charged to a flask and dissolved in DMF (50.0 mL). DIPEA (4.92 mL, 28.1 mmol) was added and the reaction was stirred overnight. The reaction was quenched with sat NH$_4$Cl and diluted with EtOAc and water. The organic phase was washed with brine, dried over MgSO$_4$ then filtered and solvent was removed. The compound purified by flash chromatography eluting with 0-5% MeOH/CH$_2$Cl$_2$ to give (3-((R)-2-((R)-2-((2-carbamoyl-4-iodophenyl)amino)-1-hydroxy-2-oxoethyl)-3-oxomorpholino)-1H-pyrazol-1-yl) methyl pivalate, as a white solid. LCMS calc.=600.10. found=600.08 (M+H$^+$).

Step 12-5: (R)-2-((S)-Hydroxy(6-iodo-4-oxo-1,4-dihydroquinazolin-2-yl)methyl)-4-(1H-pyrazol-3-yl) morpholin-3-one (Intermediate 12-5)

(3-((R)-2-((R)-2-((2-Carbamoyl-4-iodophenyl)amino)-1-hydroxy-2-oxoethyl)-3-oxomorpholino)-1H-pyrazol-1-yl) methyl pivalate (3.2 g, 5.34 mmol) was charged to a flask and dissolved in MeOH (32.0 mL). Potassium tert-butoxide (10.68 mL of a 1 M soln in t-BuOH, 10.68 mmol) was added and the reaction was stirred at room temperature for 3 h. The reaction was quenched with acetic acid (0.611 mL, 10.68 mmol). EtOAc and water were added. The organic layer was washed with sat NH$_4$Cl and brine. The organic layer was dried over MgSO$_4$, filtered and the solvent was removed to give (R)-2-((S)-hydroxy(6-iodo-4-oxo-1,4-dihydroquinazolin-2-yl)methyl)-4-(1H-pyrazol-3-yl)morpholin-3-one. This was used in the next step without further purification. LCMS calc.=468.02. found=467.90 (M+H$^+$).

Step 12-6: (R)-2-((S)-Hydroxy(6-iodo-4-oxo-1,4-dihydroquinazolin-2-yl)methyl)-4-(1-(pyridazin-4-yl)-1H-pyrazol-3-yl)morpholin-3-one (R)-2-((S)-Hydroxy(6-iodo-4-oxo-1,4-dihydroquinazolin-2-yl)methyl)-4-(1-(pyridazin-4-yl)-1H-pyrazol-3-yl) morpholin-3-one (508 mg, 1.087 mmol), 4-iodopyridazine (336 mg, 1.631 mmol), copper (I) iodide (62.1 mg, 0.326 mmol) and K$_2$CO$_3$ (301 mg, 2.175 mmol) were charged to a vial. DMSO (5080 µl) was added and the reaction was degassed (2-3 min). trans-N,N'-Dimethylcyclohexane-1,2-diamine (177 µl, 1.087 mmol) was added and the reaction was heated to 45° C. The reaction was cooled to room temperature, diluted with EtOAc and quenched with 1M AcOH. The organic layer was washed with satd NaHCO$_3$ and brine, then dried over MgSO$_4$, filtered and the solvent was removed. The compound was purified by flash chromatography eluting with 0-10% MeOH/CH$_2$Cl$_2$ to give of (R)-2-((S)-hydroxy(6-iodo-4-oxo-1,4-dihydroquinazolin-2-yl)methyl)-4-(1-(pyridazin-4-yl)-1H-pyrazol-3-yl)morpholin-3-one as a pale yellow solid. LCMS calc.=546.04. found=546.00 (M+H$^+$).

The following compounds (Table 3) were synthesized using methods analogous to those described for EXAMPLE 5 and INTERMEDIATE 12 from commercially available materials or intermediates whose syntheses are described above.

TABLE 3

| Example | | LCMS (M + H)$^+$ | Calc. (M + H)$^+$ |
|---|---|---|---|
| 6 | 2-{(S)-hydroxy[(2R)-2-methyl-3-oxo-4-{1-[6-(trifluoromethyl)pyridazin-4-yl]-1H-pyrazol-yl}morpholin-2-yl]methyl}-6-(1H-pyrazol-4-yl)quinazolin-4(1H)-one | 568.04 | 568.17 |

Example 7

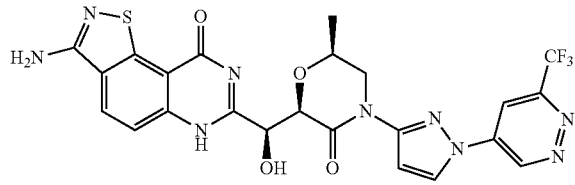 [SMILES: C[C@H]1CN(c2ccn(-c3cnnc(C(F)(F)F)c3)n2)C(=O)[C@@H]([C@@H](O)c2nc(=O)c3c(ccc4c(N)nsc43)[nH]2)O1]

(2R,6S)-2-((S)-(3-Amino-9-oxo-6,9-dihydroisothiazolo[5,4-f]quinazolin-7-yl)(hydroxy)methyl)-6-methyl-4-(1-(6-(trifluoromethyl)pyridazin-4-yl)-1H-pyrazol-3-yl)morpholin-3-one

Step 7-1: (R)-tert-Butyl 2-hydroxy-2-((2R,6S)-6-methyl-3-oxo-4-(1-(6-(trifluoromethyl)pyridazin-4-yl)-1H-pyrazol-3-yl)morpholin-2-yl)acetate (Compound 7-1)

Copper(I) iodide (14.0 mg, 0.073 mmol), potassium phosphate tribasic (104 mg, 0.489 mmol) and trans-N,N'-dimethylcyclohexane-1,2-diamine (12 µl, 0.073 mmol) were added successively to a microwave tube containing a stirred solution of (R)-tert-butyl 2-hydroxy-2-((2R,6S)-6-methyl-3-oxomorpholin-2-yl)acetate (60 mg, 0.245 mmol) and 5-(3-iodo-1H-pyrazol-1-yl)-3-(trifluoromethyl)pyridazine (125 mg, 0.367 mmol) in dry 1,4-dioxane (2.4 mL) at room temperature under $N_2$. $N_2$ was bubbled through the mixture for 5 min then the tube was sealed and heated at 80° C. overnight. The reaction was filtered through a plug of silica. The filtrate was diluted with water and extracted with EtOAc. The organic layer was dried ($Na_2SO_4$) and concentrated in vacuo to give the crude product. This was purified by flash chromatography (EtOAc/hexanes gradient from 0-50%) to afford (R)-tert-butyl 2-hydroxy-2-((2R,6S)-6-methyl-3-oxo-4-(1-(6-(trifluoromethyl)pyridazin-4-yl)-1H-pyrazol-3-yl)morpholin-2-yl)acetate. LCMS calc.=458.17. found=457.94 (M+H)$^+$.

Step 7-2: (R)-tert-Butyl 2-acetoxy-2-((2R,6S)-6-methyl-3-oxo-4-(1-(6-(trifluoromethyl)pyridazin-4-yl)-1H-pyrazol-3-yl)morpholin-2-yl)acetate (Compound 7-2)

Acetic anhydride (13 µl, 0.137 mmol), pyridine (11 µl, 0.137 mmol) and DMAP (0.8 mg, 6.86 µmol) were added to a stirred solution of (R)-tert-butyl 2-hydroxy-2-((2R,6S)-6-methyl-3-oxo-4-(1-(6-(trifluoromethyl)pyridazin-4-yl)-1H-pyrazol-3-yl)morpholin-2-yl)acetate (31.4 mg, 0.069 mmol) in dry $CH_2Cl_2$ (858 µl) at 25° C. under $N_2$ and the resulting solution was stirred at 25° C. overnight. The mixture was diluted with EtOAc and washed with a solution of aq. $CuSO_4$ followed by brine. The organic layer was dried ($Na_2SO_4$) and concentrated in vacuo to afford the crude product. This was purified by flash chromatography (ISCO, Biotage SNAP cartridge, 25 g, EtOAc/hexanes gradient from 0-50%) to afford (R)-tert-butyl 2-acetoxy-2-((2R,6S)-6-methyl-3-oxo-4-(1-(6-(trifluoromethyl)pyridazin-4-yl)-1H-pyrazol-3-yl)morpholin-2-yl)acetate. LCMS calc.=500.18. found=499.90 (M+H)$^+$.

Step 7-3: (R)-2-Acetoxy-2-((2R,6S)-6-methyl-3-oxo-4-(1-(6-(trifluoromethyl)pyridazin-4-yl)-1H-pyrazol-3-yl)morpholin-2-yl)acetic acid (compound 7-3)

(R)-tert-Butyl 2-acetoxy-2-((2R,6S)-6-methyl-3-oxo-4-(1-(6-(trifluoromethyl)pyridazin-4-yl)-1H-pyrazol-3-yl)morpholin-2-yl)acetate (48 mg, 0.096 mmol) in a mixture of $CH_2Cl_2$ (481 µl) and TFA (481 µl) was stirred at room temperature for 4 h. The mixture was concentrated in vacuo to afford (R)-2-acetoxy-2-((2R,6S)-6-methyl-3-oxo-4-(1-(6-(trifluoromethyl)pyridazin-4-yl)-1H-pyrazol-3-yl)morpholin-2-yl)acetic acid. LCMS calc.=444.11. found=443.85 (M+H)$^+$.

Step 7-4: (R)-2-((7-Carbamoyl-3-(1,3-dioxoisoindolin-2-yl)benzo[d]isothiazol-6-yl)amino)-1-((2R,6S)-6-methyl-3-oxo-4-(1-(6-(trifluoromethyl)pyridazin-4-yl)-1H-pyrazol-3-yl)morpholin-2-yl)-2-oxoethyl acetate (compound 7-4)

A mixture of thionyl chloride (690 µl, 9.47 mmol) and (R)-2-acetoxy-2-((2R,6S)-6-methyl-3-oxo-4-(1-(6-(trifluoromethyl)pyridazin-4-yl)-1H-pyrazol-3-yl)morpholin-2-yl)acetic acid (42 mg, 0.095 mmol) was heated at 50° C. for 1 h. The reaction mixture was concentrated using a stream of $N_2$. A solution of the crude acid chloride in dry $CH_2Cl_2$ (947 µl) was added via cannula to a solution of 6-amino-3-(1,3-dioxoisoindolin-2-yl)benzo[c/]isothiazole-7-carboxamide (32.1 mg, 0.095 mmol) and 4-dimethylaminopyridine (2.3 mg, 0.019 mmol) in dry pyridine (947 µl). The mixture was stirred for 2 h at 25° C. The reaction mixture was concentrated in vacuo to give the crude product. This was purified by reversed-phase HPLC (C18, 20×100 mm, ~20 mL/min, gradient from 90% water in MeCN to 40% water in MeCN over 30 min) to afford a mixture of (R)-2-((7-carbamoyl-3-(1,3-dioxoisoindolin-2-yl)benzo[d]isothiazol-6-yl)amino)-1-((2R,6S)-6-methyl-3-oxo-4-(1-(6-(trifluoromethyl)pyridazin-4-yl)-1H-pyrazol-3-yl)morpholin-2-yl)-2-oxoethyl acetate and (S)-(3-(1,3-dioxoisoindolin-2-yl)-9-oxo-6,9-dihydroisothiazolo[5,4-f]quinazolin-7-yl)((2R,6S)-6-methyl-3-oxo-4-(1-(6-(trifluoromethyl)pyridazin-4-yl)-1H-pyrazol-3-yl)morpholin-2-yl)methyl acetate. The material was carried forward as it is. LCMS calc.=764.15. found=764.32 (M+H)$^+$.

Step 7-5: (2R,6S)-2-((S)-(3-Amino-9-oxo-6,9-dihydroisothiazolo[5,4-f]quinazolin-7-yl)(hydroxy)methyl)-6-methyl-4-(1-(6-(trifluoromethyl)pyridazin-4-yl)-1H-pyrazol-3-yl)morpholin-3-one Hydrazine (16 µl, 0.498 mmol) was added to a solution of the product obtained in Step D (38 mg, 0.050 mmol) in $CH_2Cl_2$ (4.1 mL) and MeOH (4.1 mL) and the resulting mixture was stirred at 25° C. for 1 h. Ammonia (14 µl, 0.100 mmol) was added and the reaction was stirred for 4 h. The reaction mixture was concentrated in vacuo to give the crude product. This was purified by reversed-phase HPLC (C18, 20×100 mm, ~20 mL/min, gradient from 100% water in MeCN to 50% water in MeCN over 25 min, gradient to 100% MeCN over 2 min) to afford the crude material. Potassium tert-butoxide (1 M in t-BuOH) (73 µl, 0.073 mmol) was added to a solution of this material in dry MeOH (734 uL). The resulting mixture was stirred at 25° C. for 3 h. Acetic acid (4 µl, 0.073 mmol) was added and the volatiles were removed using a stream of $N_2$. The resulting residue was diluted with DMSO and purified by reversed-phase HPLC (C18, 20×100 mm, ~20 mL/min, gradient from 100% water in MeCN to 40% water in MeCN over 25 min, gradient to 100% MeCN over 2 min) to afford (2R,6S)-2-((S)-(3-amino-9-oxo-6,9-dihydroisothiazolo[5,4-f]quinazolin-7-yl)(hydroxy)methyl)-6-methyl-4-(1-(6-(trifluoromethyl)pyridazin-4-yl)-1H-pyrazol-3-yl)morpholin-3-one. LCMS calc.=574.12. found=573.95 (M+H)$^+$.

The following compounds (Table 4) were synthesized using methods analogous to those described for EXAMPLE 7 from commercially available materials or intermediates whose syntheses are described above.

TABLE 4

| Example | | LCMS (M + H)+ | Calc. (M + H)+ |
|---|---|---|---|
| 8 | 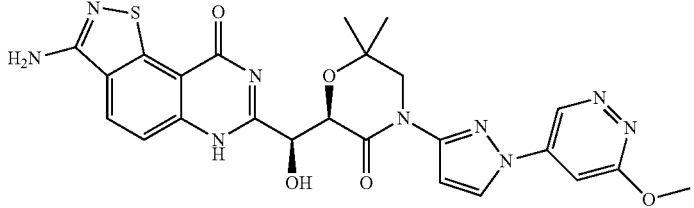 [SMILES: COc1cc(-n2ccc(N3CC(C)(C)O[C@H]([C@@H](O)c4nc(=O)c5c(ccc6c(N)nsc65)[nH]4)C3=O)n2)cnn1] (R)-2-((S)-(3-amino-9-oxo-6,9-dihydroisothiazolo[5,4-f]quinazolin-7-yl)(hydroxy)methyl)-4-(1-(6-methoxypyridazin-4-yl)-1H-pyrazol-3-yl)-6,6-dimethylmorpholin-3-one | 549.97 | 550.16 |

Determination of Inhibitory Activity Against Factor IXa

Formation of a clot to stem bleeding at a site of blood vessel injury involves the coordinated activity of a group of plasma proteins that initiate and propagate fibrin formation and subsequently protect fibrin from premature degradation. Factor IX is a key component of the plasma system that forms a fibrin clot at a site of vascular injury. The activity of Factor IXa is measured by monitoring the cleavage of the fluorescent peptide, $CH_3SO_2$-D-CHG-Gly-Arg-AFC.AcOH ("CHG" is cyclohexyl-glycine and "AFC" is trifluoro aminomethyl coumarin). Factor IXa cleaves the anode: bond between Arg and AFC, thereby releasing the AFC fluorophore. The free AFC can be detected with a fluorescence detector at an excitation wavelength of 405 nM and emission wavelength of 510 nM.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

Compounds of the Formula (I) can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor IXa inhibitors can also be co-administered with suitable anticoagulants, including, but not limited to, other Factor IXa inhibitors, thrombin inhibitors, thrombin receptor antagonists, factor VIIa inhibitors, factor Xa inhibitors, factor XIa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor IXa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor IXa inhibitors of the invention in combination with other suitable anti-platelet agents, anticoagulation agents, or thrombolytic agents may be the same as those doses of Factor IXa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

What is claimed is:
1. A compound of formula I

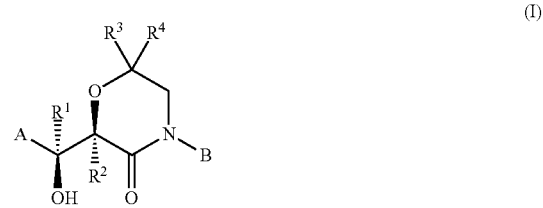

or a pharmaceutically acceptable salt thereof, wherein
$R^1$, $R^2$, $R^3$ and $R^4$ are independently H or $C_{1-6}$ alkyl, provided that when $R^1$, $R^2$, and $R^3$ are H, $R^4$ is $C_{1-6}$ alkyl, and when $R^1$, $R^2$, and $R^4$ are H, $R^3$ is $C_{1-6}$ alkyl, and when $R^1$, $R^3$, and $R^4$ are H, $R^2$ is $C_{1-6}$ alkyl, and when $R^2$, $R^3$, and $R^4$ are H, $R^1$ is $C_{1-6}$ alkyl;

A is
1) a 9-10 membered bicyclic heterocycle having 2-3 heteroatoms independently selected from N, S and O, which 9-10 membered bicyclic heterocycle is substituted with pyrazole, or
2) a 12-, 13-, or 14-membered tricyclic heterocycle having 3-5 heteroatoms selected from N, S and O, which 12-, 13-, or 14-membered heterocycle is unsubstituted or substituted with =O or $NH_2$;

B is
1) a 5-membered monocyclic heterocycle having 2 nitrogen atoms and 3 carbon atoms, where
one 5-membered monocyclic heterocycle nitrogen is substituted with 6-membered monocyclic heterocycle having one or two nitrogen atoms, $C_{1-6}$ alkyl, $C_{3-8}$ carbocycle, or aryl, wherein heterocycle, alkyl, carbocycle and aryl are unsubstituted, mono-substituted, or independently di-substituted with $CF_3$, $OCH_3$, F, CN, $-CHF_2$, or =O,
and one 5-membered monocyclic heterocycle carbon atom is unsubstituted or substituted with $C_{1-6}$ alkyl, 2) a 6-membered monocyclic heterocycle having 1 nitrogen atom and 5 carbon atoms, where one or two carbon atoms are independently unsubstituted or independently substituted with $CF_3$, —$C(CH_3)_2OH$, —$OCHF_2$, —$CH(CF_3)OH$, —$C(CF_3)(CH_3)OH$, F,

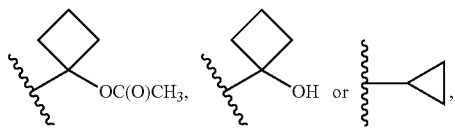

or 3) aryl, substituted with —$C_{1-6}$ alkyl.

2. A compound of claim 1, or a pharmaceutically acceptable salt thereof, wherein $R^1$, $R^2$, $R^3$ and $R^4$ are independently H or $C_{1-6}$ alkyl, provided that when $R^1$, $R^2$, and $R^3$ are H, $R^4$ is $C_{1-6}$ alkyl, and when $R^1$, $R^2$, and $R^4$ are H, $R^3$ is $C_{1-6}$ alkyl, and when $R^1$, $R^3$, and $R^4$ are H, $R^2$ is $C_{1-6}$ alkyl, and when $R^2$, $R^3$, and $R^4$ are H, $R^1$ is $C_{1-6}$ alkyl;

A has the formula (II)

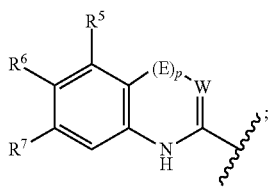

(II)

wherein

W is N or CH;

E is $S(O)_2$ or C(O);

p is 0 or 1;

$R^5$ is H or, together with $R^6$ and the atoms to which they are attached, forms a 5- or 6-membered monocyclic heterocycle having 2 heteroatoms independently selected from N, S and O, which heterocycle is substituted at a carbon atom with $NH_2$;

$R^6$ is pyrazole, or, together with $R^5$ and the atoms to which they are attached, forms a 5- or 6-membered monocyclic heterocycle, having 2 heteroatoms independently selected from N, S and O, which heterocycle is substituted at a carbon atom with $NH_2$, or, provided $R^5$ and $R^6$ do not form a heterocycle, forms, together with $R^7$ and the atoms to which they are attached, a 5-membered monocyclic heterocycle, having 2 heteroatoms independently selected from N, S and O, or forms, together with $R^7$ and the atoms to which they are attached, a 6-membered monocyclic heterocycle having 1 N atom, which 5- or 6-membered heterocycle is substituted at a carbon atom with $NH_2$;

$R^7$ is H, or, provided $R^5$ and $R^6$ do not form a heterocycle, forms, together with $R^6$ and the atoms to which they are attached, a 5-membered monocyclic heterocycle, having 2 heteroatoms independently selected from N, S and O, or forms, together with $R^6$ and the atoms to which they are attached, a 6-membered monocyclic heterocycle having 1 N atom, which 5- or 6-membered heterocycle is substituted at a carbon atom with $NH_2$; and B is 1) a 5-membered monocyclic heterocycle having 2 nitrogen atoms and 3 carbon atoms, where one 5-membered monocyclic heterocycle nitrogen is substituted with

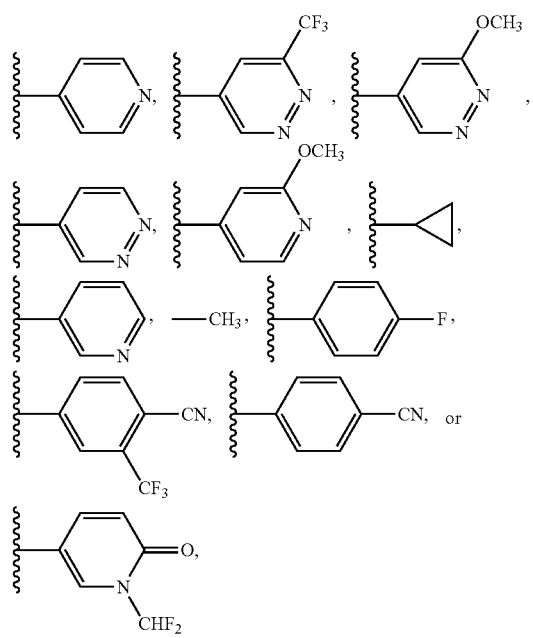

and one 5-membered monocyclic heterocycle carbon atom is unsubstituted or substituted with —$CH_3$, 2) a 6-membered monocyclic heterocycle having 1 nitrogen atom and 5 carbon atoms, where one or two carbon atoms are independently unsubstituted or independently substituted with $CF_3$, —$C(CH_3)_2OH$, —$OCHF_2$, —$CH(CF_3)OH$, —$C(CF_3)(CH_3)OH$, F,

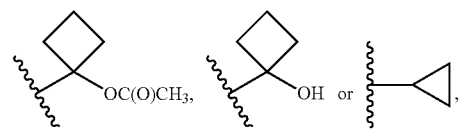

or 3) aryl, substituted with —$CH_3$.

3. A compound of claim 1, or a pharmaceutically acceptable salt thereof, wherein $R^1$, $R^2$, $R^3$ and $R^4$ are independently H or $C_{1-6}$ alkyl, provided that when $R^1$, $R^2$, and $R^3$ are H, $R^4$ is $C_{1-6}$ alkyl, and when $R^1$, $R^2$, and $R^4$ are H, $R^3$ is $C_{1-6}$ alkyl, and when $R^1$, $R^3$, and $R^4$ are H, $R^2$ is $C_{1-6}$ alkyl, and when $R^2$, $R^3$, and $R^4$ are H, $R^1$ is $C_{1-6}$ alkyl;

A is

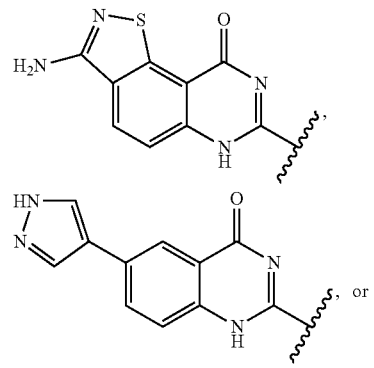

or

-continued

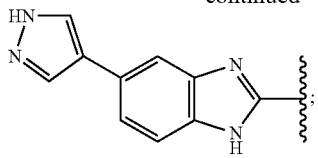

and
B is

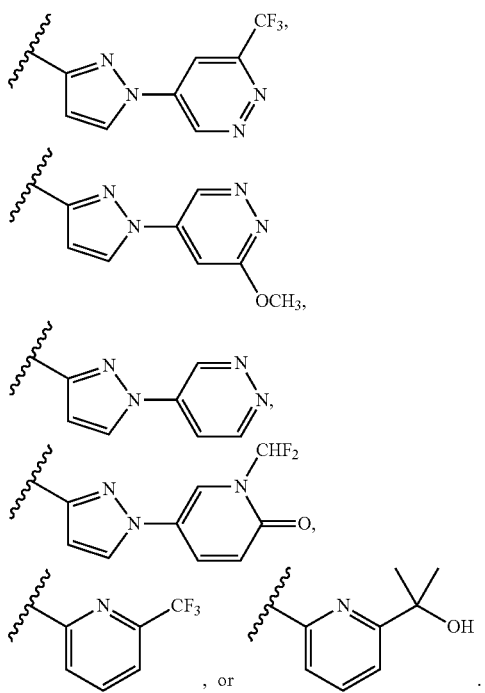

, or

4. A compound of claim 1, or a pharmaceutically acceptable salt thereof, wherein $R^1$, $R^2$, $R^3$ and $R^4$ are independently H or $CH_3$, provided that when $R^1$, $R^2$, and $R^3$ are H, $R^4$ is $CH_3$, and when $R^1$, $R^2$, and $R^4$ are H, $R^3$ is $CH_3$, and when $R^1$, $R^3$, and $R^4$ are H, $R^2$ is $CH_3$, and when $R^2$, $R^3$, and $R^4$ are H, $R^1$ is $CH_3$.

5. A compound of claim 1, or a pharmaceutically acceptable salt thereof, which is
(R)-2-((S)-(3-Amino-9-oxo-6,9-dihydroisothiazolo[5,4-f]quinazolin-7-yl)(hydroxy)methyl)-4-(1-(1-(difluoromethyl)-6-oxo-1,6-dihydropyridin-3-yl)-1H-pyrazol-3-yl)-2-methylmorpholin-3-one,
(R)-2-((S)-(3-Amino-9-oxo-6,9-dihydroisothiazolo[5,4-f]quinazolin-7-yl)(hydroxy)methyl)-2-methyl-4-(1-(pyridazin-4-yl)-1H-pyrazol-3-yl)morpholin-3-one,
(R)-2-((S)-1-(3-Amino-9-oxo-6,9-dihydroisothiazolo[5,4-f]quinazolin-7-yl)-1-hydroxyethyl)-4-(6-(trifluoromethyl)pyridin-2-yl)morpholin-3-one,
(R)-2-((S)-(3-Amino-9-oxo-6,9-dihydroisothiazolo[5,4-f]quinazolin-7-yl)(hydroxy)methyl)-4-(6-(2-hydroxypropan-2-yl)pyridin-2-yl)-2-methylmorpholin-3-one,
(R)-2-((S)-(5-(1H-Pyrazol-4-yl)-1H-benzo[d]imidazol-2-yl)(hydroxy)methyl)-6,6-dimethyl-4-(1-(6-(trifluoromethyl)pyridazin-4-yl)-1H-pyrazol-3-yl)morpholin-3-one,
2-{(S)-hydroxy[(2R)-2-methyl-3-oxo-4-{1-[6-(trifluoromethyl)pyridazin-4-yl]-1H-pyrazol-3-yl}morpholin-2-yl]methyl}-6-(1H-pyrazol-4-yl)quinazolin-4(1H)-one,
(2R,6S)-2-((S)-(3-Amino-9-oxo-6,9-dihydroisothiazolo[5,4-f]quinazolin-7-yl)(hydroxy)methyl)-6-methyl-4-(1-(6-(trifluoromethyl)pyridazin-4-yl)-1H-pyrazol-3-yl)morpholin-3-one, or
(R)-2-((S)-(3-amino-9-oxo-6,9-dihydroisothiazolo[5,4-f]quinazolin-7-yl)(hydroxy)methyl)-4-(1-(6-methoxypyridazin-4-yl)-1H-pyrazol-3-yl)-6,6-dimethylmorpholin-3-one.

6. A composition for inhibiting thrombus formation in blood comprising a compound of claim 1, or a pharmaceutically acceptable salt thereof, and a pharmaceutically acceptable carrier.

* * * * *